United States Patent
Tobinick

(10) Patent No.: US 6,595,985 B1
(45) Date of Patent: Jul. 22, 2003

(54) APPARATUS AND METHOD EMPLOYING PARAMETRICALLY DEFINED PULSE GROUPS FOR LASER HAIR REMOVAL

(76) Inventor: Edward L. Tobinick, 100 UCLA Medical Plaza, Suite 205, Los Angeles, CA (US) 90024

( * ) Notice: Subject to any disclaimer, the term of this patent is extended or adjusted under 35 U.S.C. 154(b) by 0 days.

(21) Appl. No.: 09/415,303

(22) Filed: Oct. 8, 1999

Related U.S. Application Data

(63) Continuation-in-part of application No. 09/083,482, filed on May 22, 1998.

(51) Int. Cl.[7] ............................................. A61B 18/203
(52) U.S. Cl. ................................. 606/9; 606/3; 606/13
(58) Field of Search .................................... 606/3, 9–13

(56) References Cited

U.S. PATENT DOCUMENTS

| | | | |
|---|---|---|---|
| 5,630,811 A | * 5/1997 | Miller | 606/9 |
| 6,149,645 A | * 11/2000 | Tobinick | 606/9 |
| 6,159,204 A | * 12/2000 | Hibst | 606/3 |
| 6,165,171 A | * 12/2000 | Tobinick | 606/9 |
| 6,168,589 B1 | * 1/2001 | Tobinick | 606/9 |
| 6,171,301 B1 | * 1/2001 | Nelson et al. | 606/9 |
| 6,217,572 B1 | * 4/2001 | Tobinick | 606/3 |
| 6,235,015 B1 | * 5/2001 | Mead, III et al. | 606/9 |

\* cited by examiner

*Primary Examiner*—David M. Shay
(74) *Attorney, Agent, or Firm*—Ezra Sutton

(57) ABSTRACT

A method is provided of removing hair from the skin of a patient using a laser apparatus capable of producing an emission of laser energy in the form of a group of pulses having defined parameters, being a defined pulse group, and using an optical delivery system, which includes the steps of controlling the laser apparatus in each emission of laser energy to emit a defined pulse group of 2 to 15 pulses of coherent light energy; transmitting the defined pulse group of pulses of coherent light energy through an optical delivery system to the same spot on the skin of the patient; irradiating the same spot on the skin containing the hair to be removed with the defined pulse group of coherent light energy transmitted through the optical delivery system from the laser apparatus; controlling the laser apparatus in each emission of laser energy to emit the defined pulse group through the optical delivery system, the defined pulse group having 2 to 15 pulses at a wavelength in the range of 550 to 1200 nm, each pulse at a power level in the range of 2 to 35 Joules/cm$^2$ per pulse, each pulse having a pulse duration in the range of 1.2 to 22 milliseconds per pulse, each pulse having a beam diameter on the treatment area in the range of 4 to 50 millimeters, the defined pulse group having a total fluence in the range of 4 to 100 Joules/cm$^2$, and a repetition rate of the laser apparatus between successive defined pulse groups being 500 to 2000 milliseconds; and cooling the skin during at least one delay between pulses of the defined pulse group, wherein the at least one delay between pulses is longer to accommodate the cooling step, and wherein the step of cooling is performed by spraying cryogen on the patient's skin.

50 Claims, 18 Drawing Sheets

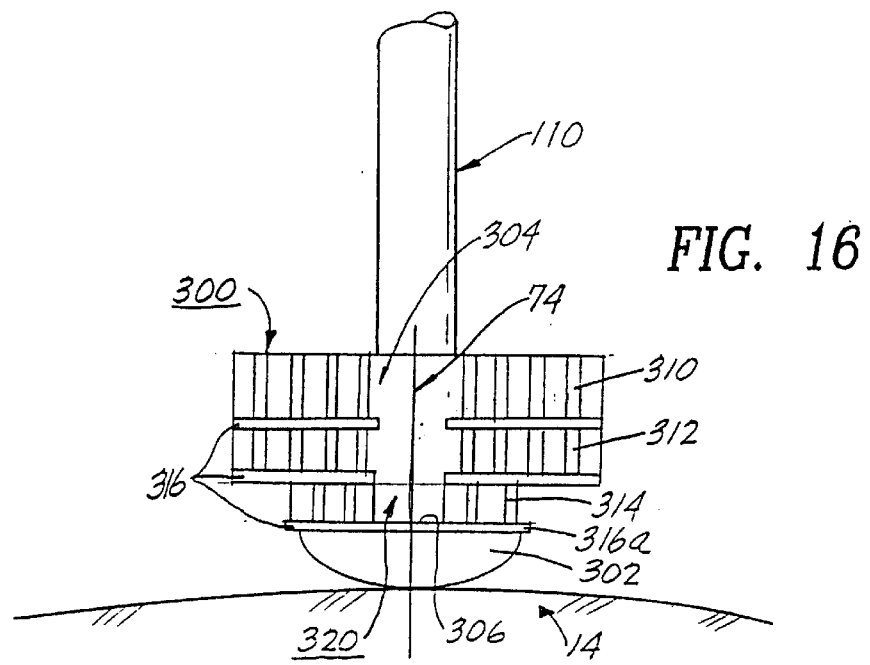
FIG. 16
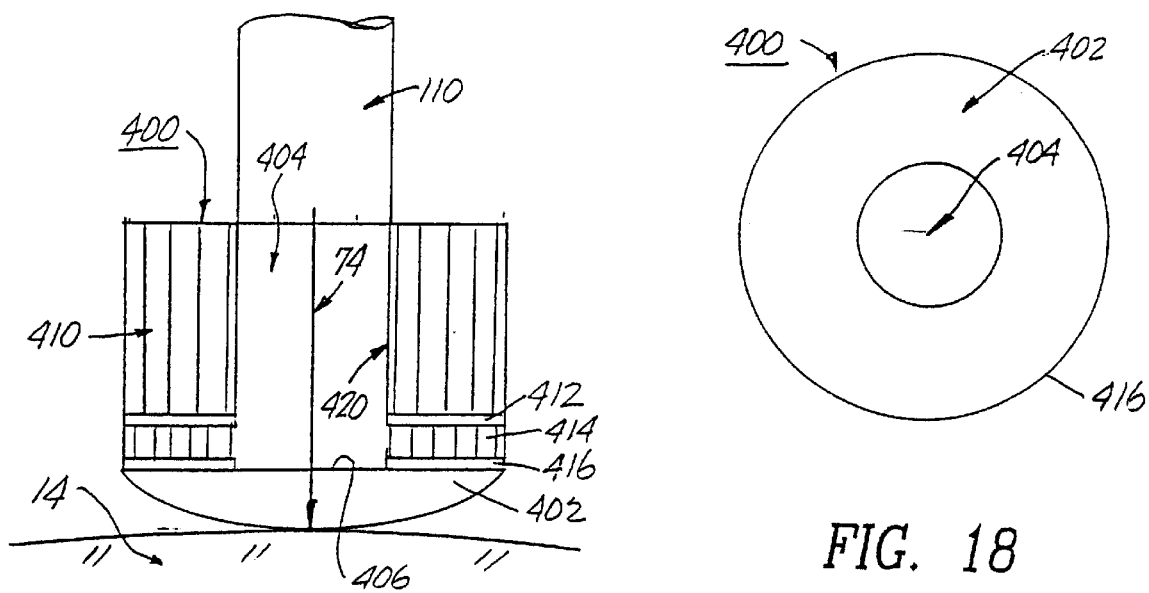
FIG. 17
FIG. 18

APPARATUS AND METHOD EMPLOYING PARAMETRICALLY DEFINED PULSE GROUPS FOR LASER HAIR REMOVAL

RELATED APPLICATION

This is a continuation-in-part of application Ser. No. 09/083,482 filed on May 22, 1998.

FIELD OF THE INVENTION

This invention relates to an improved method employing a laser apparatus for removal of hair from patients, based upon the patients' type of skin color, hair color and hair texture. More particularly, it relates to the method of using a laser apparatus to emit pulses in groups having defined parameters, each group consisting of a closely spaced (less than 20 ms between each pulse) sequence of pulses of coherent light energy (hereinafter "parametrically defined pulse groups"), which are transmitted to the same area of the skin through an optical delivery system. In this manner, the operator can control and vary the number of laser pulses, the pulse width of each pulse, the delay between each pulse, and the power level or fluence per pulse in treating a patient depending on skin color, hair color and hair texture.

BACKGROUND OF THE INVENTION

Hair removal by lasers is a new clinical field developed in the early nineties and only commercially available to patients since 1996. Lasers allow the rapid removal of large areas of hair, veins or capillaries on almost any body area, such as on the face, arms, legs, breasts, hands, stomach and the like. Laser treatment provides an unusually low discomfort level to the patient, and hair removal may last for weeks on a body area. However, all of the current lasers used for hair removal are problematic and produce unwanted side effects such as burning the skin, changes in skin pigmentation, and sometimes permanent scarring.

The currently available lasers use different approaches to hair removal, and use different laser technologies. For example, the ND:YAG laser was the first commercially available laser, but is the least effective, and does not provide permanent hair removal. The ruby laser emits a fixed wavelength of 694 nm, but has a propensity to burn the skin of the individual being treated. Because of this problem, ruby lasers cannot be used to treat olive-skinned or tanned individuals. The alexandrite laser emits a fixed wavelength of 755 nm (near the infrared spectrum), but has a propensity to burn the skin of the individual being treated, and is less effective than ruby laser treatment. Also, lasers presently being used do not consistently and reliably provide permanent hair removal, they require multiple treatments, and often burn the skin.

Pulsed flashlamps emit filtered visible light having wavelengths in the range of 550 nm and above, but have not been effective in providing permanent hair removal.

Current cutaneous lasers work by delivering energy in the form of laser light which is absorbed by the cutaneous target, heating the target and thereby causing its destruction. Different skin structures have different colors, different surface to volume configurations, and other factors which cause differential rates of heat loss. All of the hair removal lasers work by application of the principal of selective photothermoloysis, i.e. selective destruction due to heat caused by absorption of light. Laser light, which has a single wavelength, is optimally absorbed by a target which has a complementary specific color. This laser target is called a chromophore. The usual chromophore for hair removal lasers is melanin, found in high concentration in brown and black hair, and is responsible for the color of hair.

The clinical problem is that melanin is also found in the epidermis, and is responsible for native skin color and tan. Laser energy is therefore also absorbed into the epidermis. The problem of hair removal by lasers therefore is to deliver laser energy that heats the hair to a sufficient degree to cause permanent damage and hair loss, yet spare the skin of any damage. Present lasers are unable to accomplish this. For example, ruby lasers work in removing hair follicles because the wavelength of 694 nm which is emitted, is selectively absorbed by melanin and less so by other cutaneous structures, such as blood vessels. In fair skin, with little melanin, selectivity is sufficient to allow sparing of the skin and destruction of hair with even a single pulse. Alexandrite lasers perform similarly, but since their absorption by melanin is somewhat lower they seem to be less effective than ruby lasers, at least in their current forms.

The Cynosure® laser adds another approach, which they call Thermokinetic Selectivity™. This means the selective destruction of the target with the same chromophore as the skin (i.e. melanin), due to less efficient heat conduction out of the hair (as compared with the epidermis). This less efficient heat conduction is due to a variety of factors, the main one being the unfavorably large volume to surface area of the hair. The Cynosure® laser, like the ruby lasers, uses a single pulse, but the pulse used by this alexandrite laser is longer (5–20 ms). This longer pulse allows more gradual accumulation of heat by the skin, so the heat has time to dissipate (cool) and to prevent burning of the skin. This technique improves safety, but the technique is not able to deliver enough heat to provide permanent hair loss, and some burns still occur.

The use of medical lasers to produce permanent hair removal in patients with hair of all colors, and skin of all colors, has, up to this time, been impossible to achieve with current technology. While promising, the currently-used lasers have all been unable to treat patients with dark skin. In addition, even in Caucasian patients, the currently-used lasers have burned many patients, leading to prolonged changes in skin color and even, in some cases, to permanent scarring. Hair loss, although usually prolonged, has not been permanent for the majority of patients.

Nevertheless, the use of monochromatic (laser) light in the range of 694 to 900 nm still appears to be the most effective way to achieve long-term hair removal. To achieve predictable permanency we need to achieve higher temperatures in the hair without heating the epidermis to the point where it is burned. The single pulse techniques described above are inadequate to accomplish this.

There remains a need for an improved method which will supply a series of laser energy pulses with short time delays between pulses to heat a hair follicle sufficiently to cause permanent damage to that hair follicle, and yet spare the skin from burning, thus providing a safe and permanent method of hair removal for use on patients with different types of skin color, hair color and hair texture.

A new method of treatment has been developed that has the following major advantages: 1) increased efficacy, causing greater hair loss and true permanent hair removal; 2) increased safety, with burning of the skin eliminated, so that treatment has no side effects; 3) increased speed of treatment, nearly by a factor of two; 4) cooling of the skin; and 5) it allows the use of laser hair removal for patients with all skin and hair colors, thereby greatly increasing the range of people who can be treated with this technology.

DESCRIPTION OF THE PRIOR ART

Laser apparatus and methods for hair removal having various structures have been disclosed in the prior art. For example, U.S. Pat. Nos. 5,630,811 and 5,658,323 to Miller disclose a method and apparatus for dermatology treatments for lesions and hair removal using a modified laser device. The specific target for the laser radiation is the melanin within the hair shaft and within the melanocytes lining of the follicular duct. Pulse width is controlled to provide a direct thermal effect from a single pulse.

U.S. Pat. No. 5,647,866 to Zaias discloses a method of hair depilation through the application of pulsed laser energy having a wavelength readily absorbed by hemoglobin. The process of selective photothermoloysis is used by the laser to focus on a particular region in the epidermis to be irradiated. The pulse duration or time period (30 to 40 nanoseconds) is shorter than the thermal relaxation time for melanin in hair.

U.S. Pat. No. 5,683,380 to Eckhouse discloses a method and apparatus for removing hair (depilation) using a single high intensity pulsed flashlamp (not a laser) which emits a broad spectrum of pulsed incoherent light that is polychromatic. Because of the broad spectrum of wavelengths emitted by the flashlamp, only part of the light energy is absorbed by the hair, making it inefficient for permanent hair removal, although it does provide temporary hair loss.

U.S. Pat. No. 5,595,568 to Anderson et al discloses a method for permanent hair removal from a skin region of a patient using a single laser with a single pulse. This prior art patent does not teach or disclose defined pulse groups from a laser apparatus as in the present invention.

U.S. Pat. No. 5,735,844 by Anderson discloses a method for hair removal using optical pulses. The method involves using a cooled contact applicator and a single pulse. Unlike the present invention there is no disclosure of defined pulse groups (multipulsing) to the same location, with each group consisting of a closely spaced sequence of pulses, delivered to the same area of the skin (multipulsing). Nor is there any mention of a method to adjust the parameters of a defined pulse group according to skin color, hair color, and hair diameter in order to achieve safe and effective permanent hair removal. A single pulse method, as disclosed by Anderson, has a propensity to burn the skin and is unable to deliver the amount of energy that can be safely delivered by the present invention. Additionally, the present invention does not require a cooled contact applicator which is an integral part of the method disclosed by Anderson.

U.S. Pat. No. 5,752,948 to Tankovich discloses a laser hair removal method utilizing a Nd:Yag laser operating at 1.06 micron wavelength and with a pulse duration of 10 to 50 nanoseconds. This pulse duration is too short to be effective, and much shorter than that disclosed in the present invention. A pulse duration of 1.2 ms or greater is necessary to achieve permanent damage to the hair germinative apparatus. The use of Nd:Yag lasers with this short pulse duration has failed to accomplish long-term hair removal and has largely been abandoned by the medical community.

U.S. Pat. No. 5,814,040 to Nelson et al discloses a method and apparatus for dynamic cooling of biological tissues for thermal medicated surgery. The method employs dynamic cooling of the epidermal tissue with a cryogen spray. However, the cooling is applied before the laser pulse and no intra-pulse cooling occurs.

U.S. Pat. No. 5,879,346 to Waldman et al discloses a treatment method of hair removal by selective photothermolysis with an Alexandrite laser. However, there is no use of multiple pulses as in the present invention.

U.S. Pat. No. 5,885,273 to Eckhouse et al discloses a method for depilation using pulsed electromagnetic radiation. This method employs the use of a flashlamp (or incoherent light) wherein the present invention uses a laser apparatus.

U.S. Pat. No. 5,871,479 to Furomoto et al discloses a method and apparatus for hair removal using an Alexandrite laser system. However, this method has no mention of treatment for light and dark skin patients, nor any mention of cooling the patient's skin during treatment.

None of these prior art patents disclose the particular structure of the present invention or a method of using a laser apparatus to emit a closely spaced pulse sequence (multipulsing) with proper parameters for safe and permanent hair removal for use on patients with different skin colors, hair colors and hair textures.

Accordingly, it is an object of the present invention to provide an improved laser apparatus and method which supplies a defined pulse group of laser energy with short delays between the pulses from a laser apparatus to heat a hair follicle and hair follicle shaft to cause permanent damage to that hair follicle and shaft, and yet spare the skin from burning, thus providing a safe and permanent method of hair removal for patients with different skin colors, hair colors and hair textures.

Another object of the present invention is to provide an improved laser apparatus, controlled by a sequence control device, and a fiber optic cable which sequentially emits a defined pulse group having pulses of coherent light energy from the fiber optic cable for permanently removing a plurality of hair follicles from the skin area of a patient.

Another object of the present invention is to provide an improved laser apparatus having a handpiece for ease of use by the operator in directing the defined pulse group of laser pulses at the skin to rapidly remove large areas of hair on almost any body area, such as on the face, hands, arms, legs, breasts, stomach and the like, where such treatment provides a low discomfort level to the patient.

Another object of the present invention is to provide a laser apparatus and a sequence control device for emitting laser energy through an optical delivery system which delivers a defined pulse group of sequential pulses from the laser apparatus.

Another object of the present invention is to provide an improved method for adjusting the defined pulse group with regard to the numbers of pulses, the pulse width, the time delay between pulses, and the energy level of each pulse, to customize treatment and the energy delivered to the spot being treated according to skin color, hair color, hair texture (diameter) and the anatomic site being treated.

Another object of the present invention is to provide safe and permanent hair removal in a wider range of patients having different skin colors, such as a light skin color for Caucasians, a medium skin color for Hispanics, American Indians, Eastern Mediterranean-types, and a dark skin color for Africans and Afro-Americans.

Another object of the present invention is to provide safe and permanent hair removal in a wider range of patients having different hair colors and different hair textures. Such hair colors include gray and white hair; blond hair; red hair; light, medium and dark brown hair; and black hair; and having hair texture (diameter) of fine or coarse hair. Generally, the present invention will accommodate all persons having hair which is darker than their skin.

Another object of the present invention is to provide a delay between laser pulses which is much shorter than the thermal relaxation time of the hair being treated, so the hair does not cool off between pulses.

Another object of the present invention is to provide a method and laser apparatus wherein the delay between laser pulses is so short that less energy has to be transmitted to the hair to cause permanent hair loss.

Another object of the present invention is to provide an improved laser apparatus and method that is easy to use, and the laser apparatus is durable, light-weight and easily maintained.

Another object of the present invention is to provide an improved laser apparatus that provides a wider beam area (spot size on the skin) by utilizing a laser apparatus and a sequence control device for delivering enough laser energy to each spot allowing the spot size to be made larger for faster treatment.

Another object of the parametrically defined pulse group (PDPG) of the present invention is that it provides for laser hair removal to be successful in clinical situations where it previously was impossible; and it allows for both greater efficacy and greater safety by taking advantage of thermodynamic differences between hair follicles and epidermis when both are simultaneously irradiated by the laser apparatus.

A further object of the present invention is to provide an improved laser apparatus that is simple to manufacture and assemble in an economical manner, and is cost effective for the user.

SUMMARY OF THE INVENTION

In accordance with the present invention, there is provided an improved method employing a laser apparatus and a sequence control device to emit groups of pulses, each pulse group consisting of a closely spaced sequence of pulses for permanently, safely and quickly removing a plurality of hair follicles from the skin of a patient, based upon the patients' type of skin color, hair color and hair texture. These include patients having light, medium and dark skin color, and with hair colors that include light and medium brown hair, and black hair; and having fine or coarse hair texture.

A method is provided of removing hair from the skin of a patient using a laser apparatus capable of producing an emission of laser energy in the form of a group of pulses having defined parameters, being a defined pulse group, and using an optical delivery system, which includes the steps of controlling the laser apparatus in each emission of laser energy to emit a defined pulse group of 2 to 20 pulses of coherent light energy; transmitting the defined pulse group of pulses of coherent light energy through an optical delivery system to the same spot on the skin of the patient; irradiating the same spot on the skin containing the hair to be removed with the defined pulse group of coherent light energy transmitted through the optical delivery system from the laser apparatus; controlling the laser apparatus in each emission of laser energy to emit the defined pulse group through the optical delivery system, the defined pulse group having 2 to 15 pulses at a wavelength in the range of 550 to 1200 nm, each pulse at a power level in the range of 2 to 35 Joules/cm$^2$ per pulse, each pulse having a pulse duration in the range of 1.2 to 22 milliseconds per pulse, each pulse having a beam diameter on the treatment area in the range of 4 to 50 millimeters, the defined pulse group having a total fluence in the range of 4 to 100 Joules/cm$^2$, and a repetition rate of the laser apparatus between successive defined pulse groups being 500 to 2000 milliseconds; and cooling the skin during at least one delay between pulses of the defined pulse group, wherein the at least one delay between pulses is longer to accommodate the cooling step, and wherein the step of cooling is performed by spraying cryogen on the patient's skin. Additional cooling may also be performed before and/or after the defined pulse group.

Alternatively, an optional method for cooling the skin is using a thermoelectric device within the laser handpiece that includes a sapphire crystal which engages the skin area of the patient. The cooling temperature of the skin when using the thermoelectric device is in the temperature range of $-30°$ C. to $0°$ C. having a pulsing range of $\frac{1}{4}$ second to 2 seconds, with a preferable pulse being 2 seconds. The cooling may be performed before, during and/or after the defined pulse group.

The new technology requires that a series of relatively low energy laser pulses be delivered in rapid succession with short delays between pulses to exactly the same area of the skin, so that the hair does not have time to dissipate the heat between pulses. Relatively low energy per pulse is delivered to the hair germinative apparatus using a series of short pulses from the laser apparatus, with the pulses repeated at short intervals so the hair does not have time to dissipate the heat energy between pulses. For most patients, this means five or less low-energy ($1\frac{1}{2}$ to 25 Joules/cm$^2$), medium duration (2 to 6 milliseconds) pulses, separated by short delays of less than 20 milliseconds, each with a large (e.g. 10 millimeters or greater) spot size. None of the currently-produced lasers are able to produce these results. The short delay between pulses is shorter than the thermal relaxation time of the hair being treated, so the hair does not cool off between the pulses. Selective cooling of the epidermis, while not always necessary with the present invention, will be helpful to prevent epidermal damage and will allow greater laser energy to be delivered to the skin and hair. The method of epidermal cooling will impact upon the epidermal response to any given pulse sequence. Epidermal cooling may be passive, or may be done actively. Active epidermal cooling can be accomplished with ice, cold, clear ultrasound gel, or with a cooled contact applicator as disclosed by Chess in U.S. Pat. No. 5,057,104, with a thermoelectric applicator, or with cryogen spray. Individual pulse sequence parameters, particularly the delay between pulses and the total fluence delivered, will vary according to the method and the amount of epidermal cooling applied prior to, and/or during, and/or after the exposure of the skin to the laser pulse sequence.

For example, short pulse duration lasers (with a pulse duration measured in nanoseconds) can repeat rapidly, but these are too short and are not suitable for optimal hair removal. A temperature of 70 degree ° C. sustained for 1 ms or longer at the hair germinative apparatus is necessary to accomplish permanent hair removal. This requires a laser with a pulse duration of 1.2 ms or longer. All of the new hair removal lasers (ruby, alexandrite, diode) are long pulse lasers. Most of these recycle every 1000 milliseconds, with the fastest recycling every 100 milliseconds. The repetition rate that is necessary, however, must be a delay between pulses of less than 20 milliseconds. The new laser apparatus of the present invention is able to accomplish this new method.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein:

FIG. 16 is an enlarged cross-sectional view of the laser apparatus of the present invention showing a first thermoelectric cooling device connected to the laser handpiece in operational use on a patient's skin;

FIG. 17 is an enlarged cross-sectional view of the laser apparatus of the present invention showing a second thermoelectric cooling device connected to the laser handpiece in operational use on a patient's skin;

FIG. 18 is an enlarged end plan view of the laser apparatus of the present invention showing the second thermoelectric cooling device having a sapphire crystal thereon;

DETAILED DESCRIPTION OF THE PREFERRED EMBODIMENT

Figure 1:
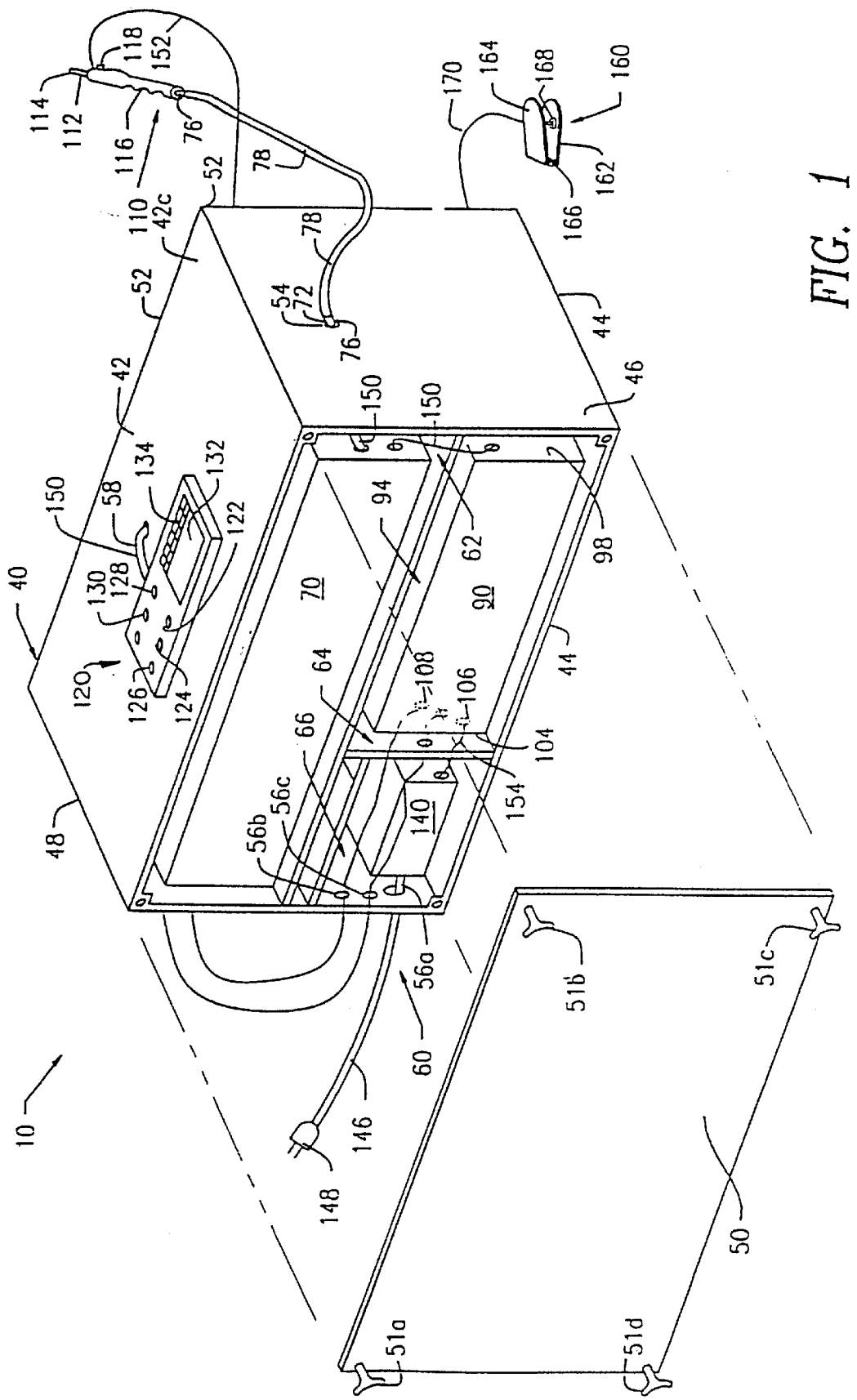
FIG. 1 is a perspective view of the laser apparatus of the preferred embodiment of the present invention showing the housing, having a control panel thereon, the single laser, the flexible conduit having a fiber optic bundle therein, the laser handpiece having thereon an operating pulse firing button, and the foot pedal switch assembly having an activation firing button thereon, shown in an operational mode.
Figure 1A:
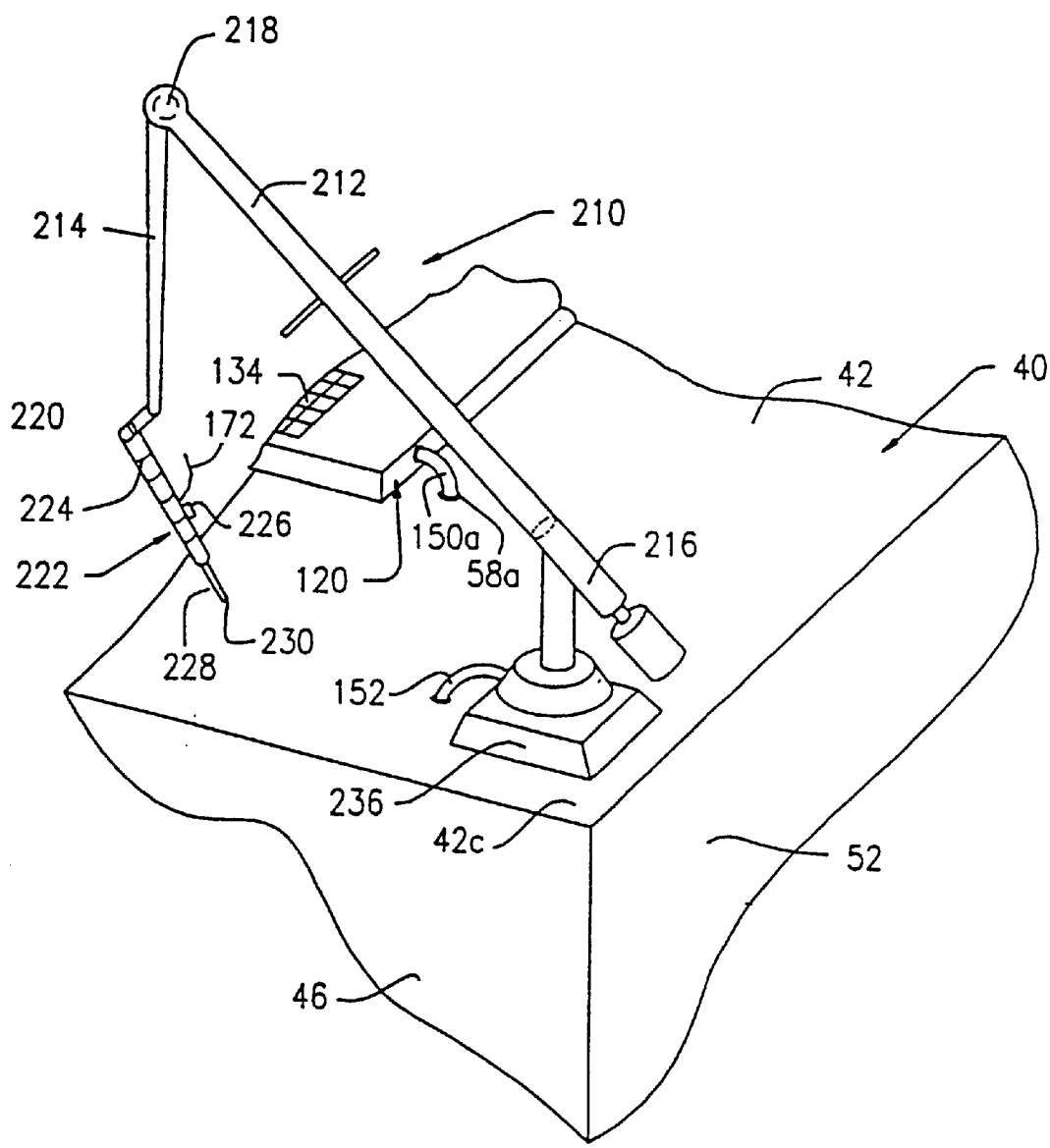
FIG. 1A is a perspective view of the laser apparatus of the present invention showing the alternate embodiment of the articulated laser arm assembly and its component parts thereon.
Figure 2:
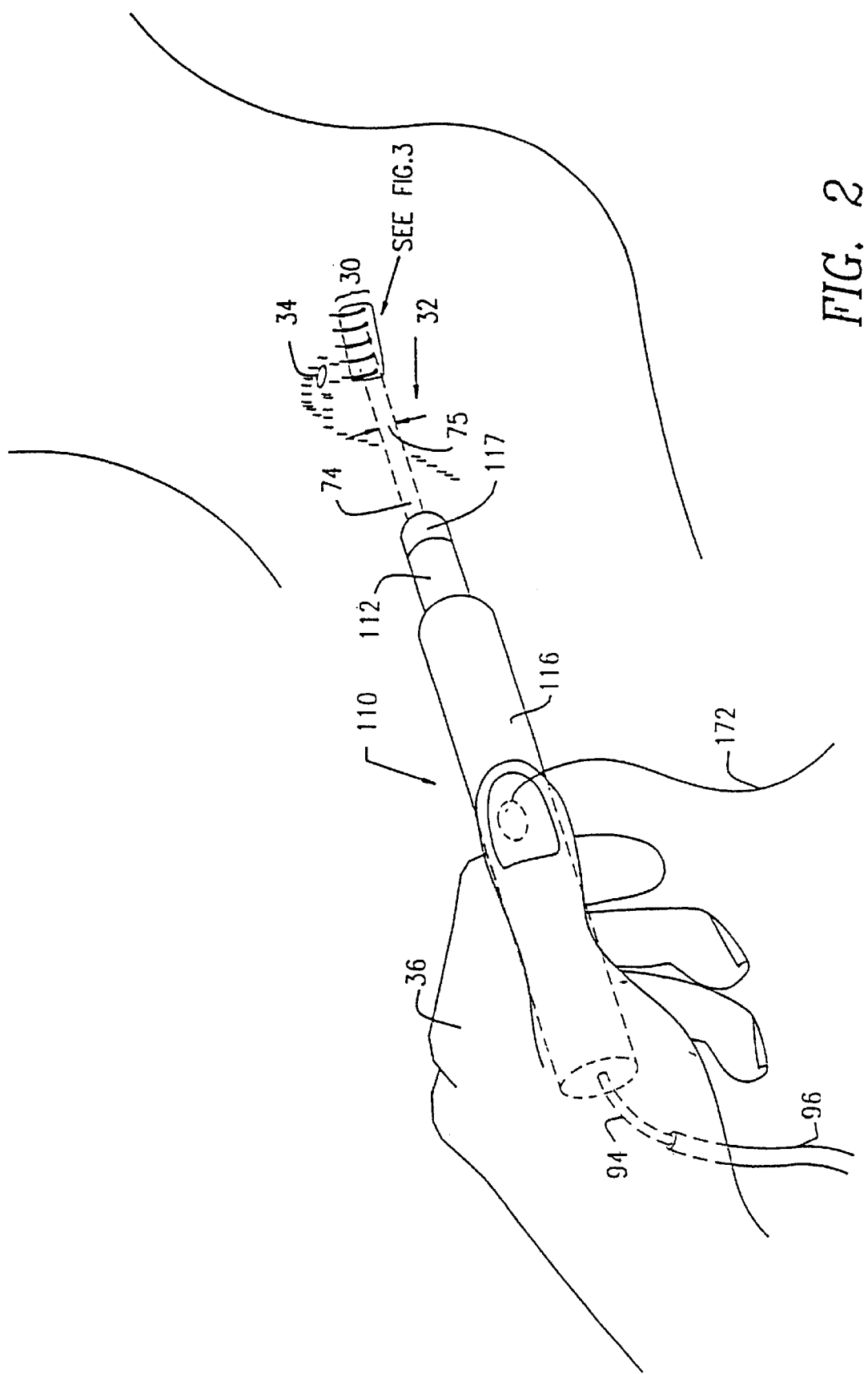
FIG. 2 is an enlarged perspective view of the laser apparatus of the present invention showing the flexible conduit and the laser handpiece having a pulse firing button thereon, shown in an operational mode.

The improved laser apparatus 10 and method for permanently removing a plurality of hair follicles 20 from a patient's skin area 14 are represented in detail by FIGS. 1, 1A, 2 through 15. The laser apparatus 10 of the present invention, as shown in FIGS. 1 and 2 of the drawings, includes a laser housing 40 having therein a laser device 70, a sequence control device 90 and an electrical panel box 160. Additionally, laser apparatus 10 also includes an optical delivery system having fiber optic bundle 76 connected to the laser device 70. Fiber optic bundle 76 is connected to a laser handpiece 110 having a pulse firing button 118 thereon. Handpiece 110 is attached at one end 95a to the fiber optic bundle 76.

Laser housing 40, as shown in FIG. 1, includes a top wall 42, a bottom wall 44, a front wall 46, a rear wall 48, and side walls 50 and 52, all being integrally connected to form a substantially rectangular shaped configuration which forms an interior chamber 60. The interior chamber 60 includes a first compartment 62 for holding and containing therein the single laser device 70, a second compartment 64 for holding and containing therein the sequence control device 90 and a third compartment 66 for holding and containing therein the electrical panel box 140.

Figure 6:
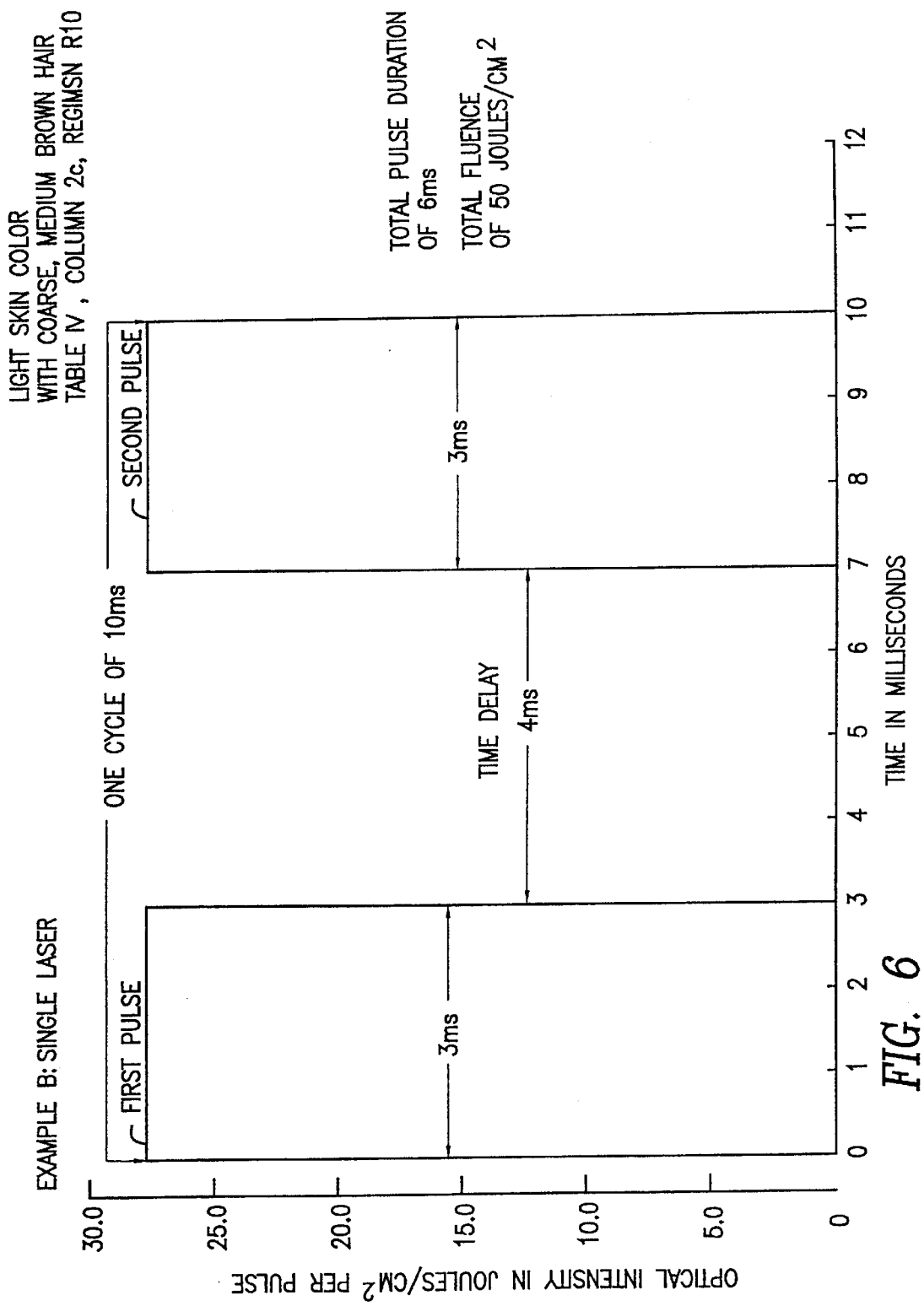
FIG. 6 is a graph showing the time profile and the optical intensity field performance for the sequential pulsing of coherent light energy of a single laser for the hair removal process and treatment of a patient having light skin color with coarse, medium brown hair.
Figure 7:
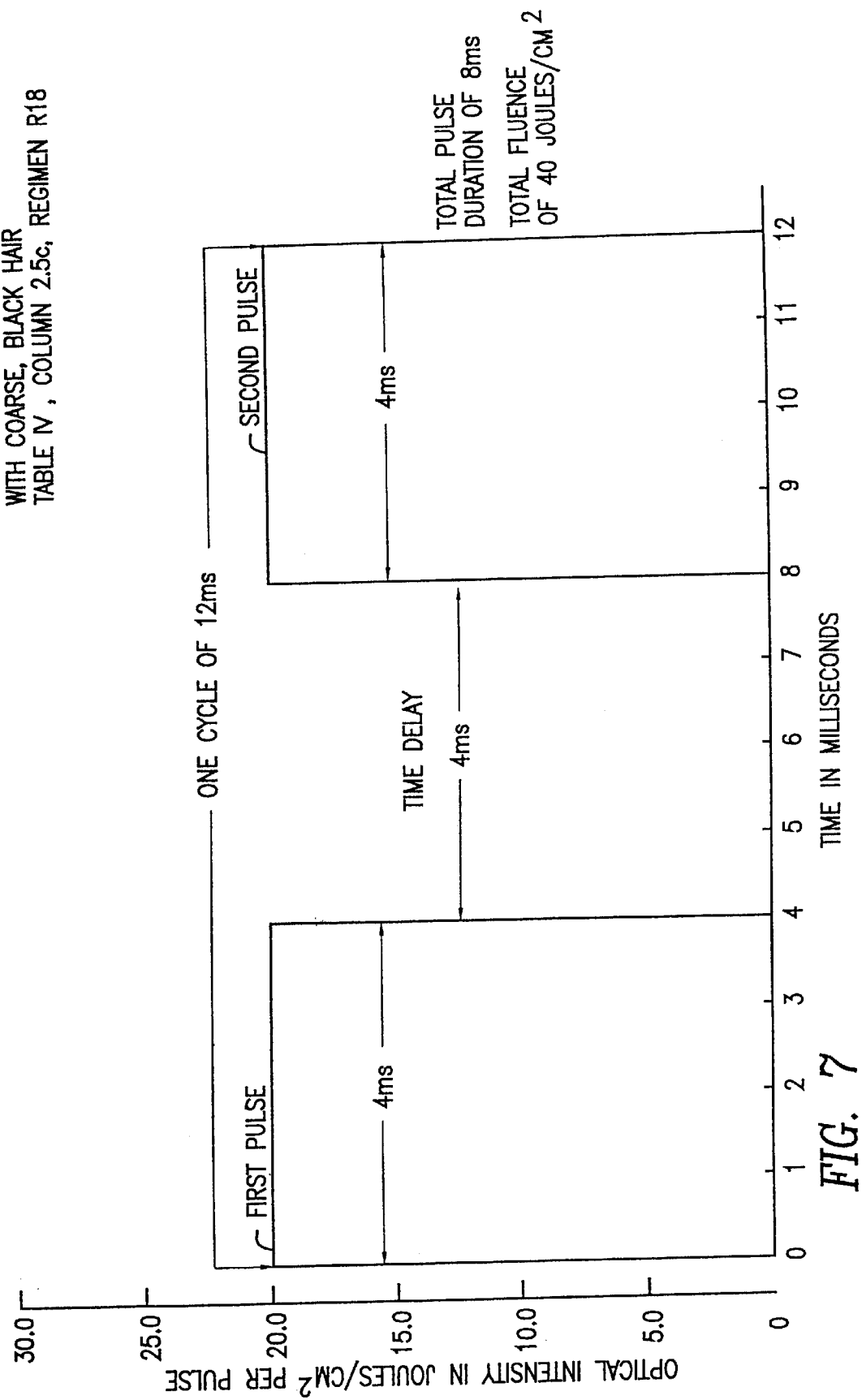
FIG. 7 is a graph showing the time profile and the optical intensity field performance for the sequential pulsing of coherent light energy of a single laser for the hair removal process and treatment of a patient having light skin color with coarse, black hair.

Single laser device 70, as shown in FIG. 1, includes a laser projector lens 72 for transmitting the coherent laser beam 74 of a specific wavelength having a laser beam diameter 75 of a given width. The laser projector lens 72 is attached to the fiber optic bundle 76 for transmitting pulses of coherent light energy (laser beam 74) from the single laser device 70 through the fiber optic bundle 76. Single laser device 70 is electrically connected to the laser sequence control device 90, to the laser programmable control panel 120, and to the electrical panel box 140 via electrical lines 142, 150, and 144, respectively, as shown in FIG. 6.

The control panel 120 controls single laser device 70 to adjust energy level (Joules/cm$^2$), pulse width duration (ms), delay time between pulses (ms), spot size (mm) and wavelength (nm).

Laser device 70 may be selected from the group consisting of an Alexandrite laser, a ruby laser, a diode laser, an infrared laser, an ND:YAG laser, an eximer pumped dye laser, an argon pumped dye laser, and the like. An alexandrite laser has a specific wavelength of 755 nm; a ruby laser has a specific wavelength of 694 nm; a pumped dye laser or a diode laser can be set at any wavelength in the range of 550 to 900 nm; and an ND:YAG laser has a specific wavelength of 1064 nm. The most effective wavelengths for permanent hair removal are in the range of 550 nm to 900 nm when using the alexandrite, ruby, diode or dye laser.

Figure 3:
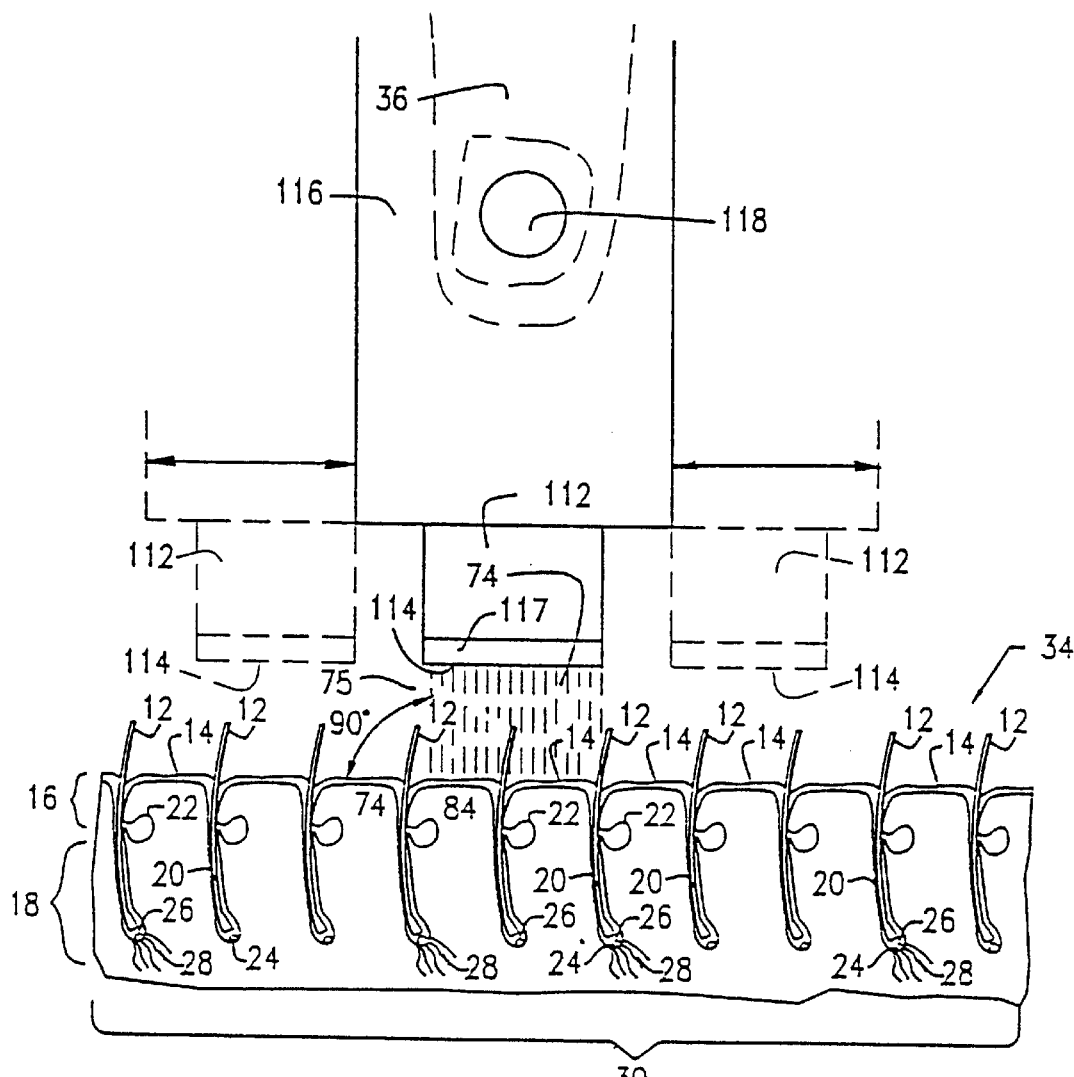
FIG. 3 is a cross-sectional view of a plurality of hair shafts within a region of skin tissue being irradiated with a laser beam from the laser handpiece of the present invention.

The laser sequence control device 90 is used for controlling the sequential pulsing of the laser beam 74 from laser device 70 to produce the defined pulse group, and includes a sequencer laser control module 92 for controlling the laser 70 to sequentially emit a series of pulses of coherent light energy when the laser operator depresses the pulse firing button 118 on laser handpiece 110. The sequencer laser control module 92 may be in the form of a microprocessor or an electronic timing device. The series of pulsed laser beams 74 will destroy and permanently remove the plurality of hair follicles 20 from the skin area 14 of a patient, as shown in FIGS. 1 to 3 of the drawings. The laser sequence control device 90 includes a substantially rectangular shaped housing 94 for holding the sequencer laser control module 92 therein. Housing 94 includes a front wall 98 with openings 100 for receiving electrical line 142 from laser device 70, such that electrical line 142 is connected to the sequencer laser control module 92; and includes a rear wall 104 having an opening 106 for receiving an electrical line 154, such that electrical line 154 connects the electrical panel box 140 to the sequencer laser control module 92, and having an opening 108 for receiving of electrical line 152, such that electrical line 152 connects the pulse firing button 118 to the sequencer laser control module 92.

As shown in FIG. 1, the front wall 46 of housing 40 includes an opening 54 for receiving the fiber optic bundle 76 from laser device 70. The rear wall 48 includes a first opening 56$a$ for receiving power line 146 connected to the electrical panel box 140, a second opening 56$b$ for receiving electrical line 152 from the pulse firing button 118 to the sequencer control module 92 of laser sequence control device 90, and a third opening 56$c$ for receiving electrical line 170 from the activation laser switch/button 168 of the foot pedal switch assembly 160 to the sequencer control module 92 of laser control device 90. Top wall 42 includes control panel 120, as well as an opening 58 for receiving an electrical line 150 from laser device 70. The left side wall 50 is removably connected to laser housing 40 via connecting means 51$a$ to 51$d$ and is used as an access panel 50 for ease of access by the laser operator for repairing and maintaining the laser device 70, the sequence control device 90 and the electrical panel box 140 thereof.

The optical delivery system includes a laser handpiece 110 used for delivering and emitting the series of sequentially pulsed laser beam 74 from laser device 70, via sequencer control module 92 of sequence control device 90. Laser handpiece 110 includes a laser dispersal member 112 having a laser portal opening 114 for receiving fiber optic bundle 76 and a lens 117 for emitting the laser beams 74 of laser device 70. Laser handpiece 110 further includes a hand gripping/holding section 116 having a pulse firing button 118 thereon. Pulse firing button 118 is electrically connected to the sequencer control module 92 of sequence control device 90 via electrical line 152. In addition, laser handpiece 110 is attached at end 95$a$ to fiber optic bundle 76. The fiber optic bundle 74 is sheathed within a flexible conduit 78 for protecting the fiber optic bundle 76.

An alternate optical delivery system is available in the form of an articulated laser arm assembly 210 and may be used in place of the fiber optic bundle 76 connected to laser device 70, and laser handpiece 110. The articulated laser arm assembly 210 is also used for transmitting the series of sequentially pulsed laser beams 74 from laser device 70. Sequence control device 90 operates in the same manner as in the preferred embodiment. The articulated laser arm assembly 210 is located on the corner section 42$c$ of top wall 42 and is adjacent to the laser control panel 120 of laser housing 40, as depicted in FIG. 1A of the drawings. Articulated laser arm assembly 210, as shown in FIG. 1A, includes a first arm member 212 pivotally attached to a second arm member 214. As is know in the art, articulated laser arm assembly 210 further includes a first mirror 216, a second mirror 218 and a third mirror 220 for reflecting the series of sequential coherent light beams (laser beams 74) through the first and second arm members 212 and 214, respectively. Additionally, articulated laser arm assembly 210, also includes a laser handle member 222 pivotally attached to the second arm member 214. Laser handle member 222 includes a gripping/holding section 224 having a pulse firing button 226 thereon, and a laser dispersal member 228 having a laser portal opening 230 for emitting the series of pulsed laser beams 74 of laser device 70. The articulated laser arm assembly 210 further includes a base member 236 for attaching to the corner section 42$c$ of top wall 42. Pulse firing button 226 is electrically connected to the sequencer control module 92 of sequence control device 90 via electrical line 152.

Another optical delivery system which may be used is a lens system connected to a common optical delivery path connected to the handpiece. In this arrangement, the output of laser 70 is directed to an angled lens which directs the light to the common optical delivery path. Other optical delivery systems, such as a light path or pipe for a diode laser, may be used.

Figure 15:
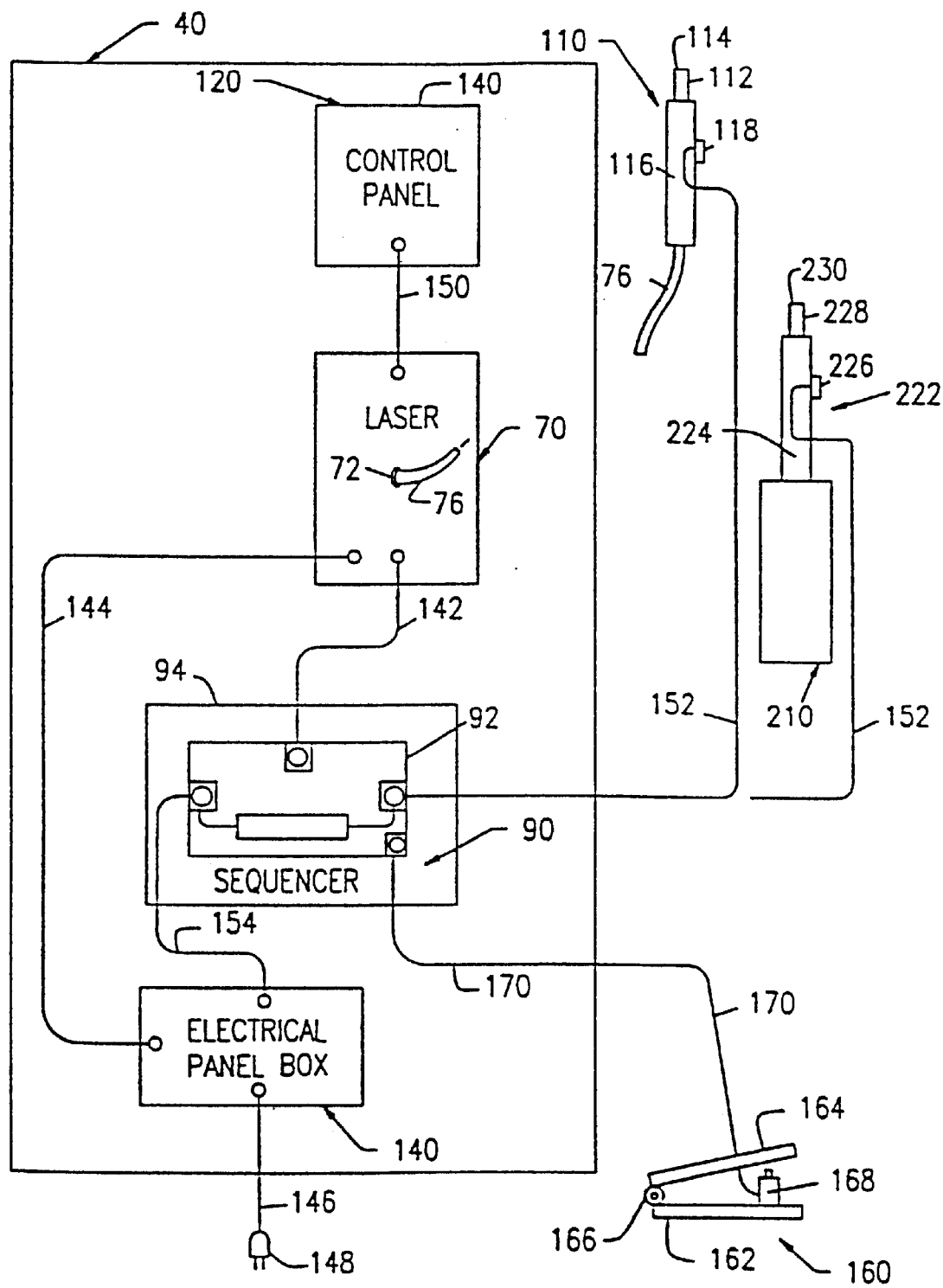
FIG. 15 is an electrical schematic block diagram of the laser apparatus of the present invention showing the electrical connections of the major component parts therein.

As shown in FIG. 15, laser device 70 is electrically connected to the sequencer laser control module 92 of laser sequence control device 90 via electrical line 142, as well as to the electrical panel box 140 via electrical line 144. Electrical power line 146 and plug 148 for a wall electrical outlet (not shown) are connected to the electrical panel box 140 via power line 146. Laser device 70 is also electrically connected via electrical line 150 to the laser programmable control panel 120. The pulse firing button 118 of laser handpiece 110 is electrically connected to the sequencer laser control module 92 via electrical line 152.

The activation laser switch/button 168 of foot pedal switch assembly 160 is electrically connected to the sequencer laser control module 92 via electrical line 170. The sequencer laser control module 92 is electrically connected to the electrical panel box 140 via electrical line 154.

The laser programmable control panel 120 is used for controlling the various output functions of energy/power level, in Joules/centimeters$^2$ (J/cm$^2$), the irradiation pulse width duration in milliseconds (ms)k, the pulse delay in milliseconds (ms), the number of pulses, and the laser beam diameter in millimeters (mm) for the single laser device 70. Control panel 120 includes a plurality of control members 122 to 130 and a visual display screen 132 having a keyboard 134 for programming the aforementioned output functions of energy/power level, pulse width duration, pulse delay, the number of pulses, and laser beam diameter 75. The control members include an ON/OFF button 122 for activating and deactivating the laser device 70; a control knob/selector 124 for adjusting the energy/power level of the laser device 70; a control knob/selector 126 for adjusting the irradiation pulse width duration (ms) of laser beam 74 of the laser device 70; a control knob/selector 128 for adjusting the pulse delay of the deactivation time (ms) of laser beam 74 of the laser device 70; and a control knob/selector 130 for adjusting the laser beam diameter 75 of the laser device 70. Control panel 120 is electrically connected to laser device 70 via electrical line 150, as shown in FIG. 15.

As an alternate to the pulse firing button 118, a foot pedal switch assembly 160 may be used for initiating the firing sequence of the series of laser beam 74 from laser device 70. Foot pedal switch assembly 160, as shown in FIG. 1 of the drawings, includes a foot pedal base 162 and a foot pedal 164 being connected to the base 162 by a hinge 166. Foot pedal base 162 includes an activation laser switch/button 168 being electrically connected to the sequencer control module 92 via electrical line 170.

Laser handpiece 110 may include an optional cooling device 300, as shown in FIG. 16 of the drawings. The cooling device 300 may include a thermoelectric device or a semi-conductor device for providing the cooling effect for device 300. Laser handpiece 110 is connected to cooling device 300 which includes a central opening 304 through which the laser pulses or beams 74 passes to the skin surface 14. Cooling device 300 includes a sapphire crystal 302 that engages the skin area 14 of the patient. The thermoelectric cooling device 300 further includes a heat sink 310, a first row of semi-conductor pellets 312, and a second row of semi-conductor pellets 314. A plurality of ceramic spacers 316 separate the heat sink 310, the first and second rows of semi-conductor pellets 312 and 314 and the sapphire crystal 302 from each other, as depicted in FIG. 16. Heat sink 310, and the first and second rows of semi-conductor pellets 312 and 314, respectively, surround an evacuated sealed chamber 320. The rear surface wall 306 of sapphire crystal 302 is adjacent and in contact with the ceramic spacer 316a, and rear surface wall 306 is also covering the central opening 304 through which laser beams 74 passes through the sapphire crystal 302 onto the skin surface 14. The cooling temperature of the skin 14 when using cooling device 300 is in the temperature range of −30° C. to 0° C. having a pulsing range of ¼ seconds to 2 seconds with a preferable pulse of 2 seconds.

Laser handpiece 110 may also include a second optional cooling device 400, as shown in FIGS. 17 and 18 of the drawings. The cooling device 400 may also include a thermoelectric device or a semi-conductor device for providing the cooling effect for device 400. Laser handpiece 110 is connected to cooling device 400 which includes a central opening 404 through which laser beams 74 passes to the skin surface 14. Cooling device 400 includes a sapphire crystal 402 that engages the skin area 14 of the patient. The thermoelectric cooling device 400 further includes a heat sink 410, a first ceramic spacer (hot side) 412, a row of semi-conductor pellets 414 and a second ceramic spacer (cool side) 416. Heat sink 410, spacer 412, semi-conductor pellets 414 and spacer 416, respectively, surround an evacuated sealed chamber 420. The rear surface wall 406 of sapphire crystal 402 is adjacent and in contact with the second ceramic spacer (cool side) 416, and also covering the central opening 404 through which laser beams 74 passes through the sapphire crystal 402 onto skin surface 14. The cooling temperature of the skin 14 when using cooling device 400 is in the temperature range of −30° C. to 0° C. having a pulsing range of ¼ seconds to 2 seconds with a preferable pulse of 2 seconds.

Other alternate methods may be used in cooling down the patient's skin 14 just prior to the laser beams 74 irradiating the patient's skin 14. For example, ice or a cooling gel can be applied to the patient's skin 14 for cooling the skin 14 down to a temperature of 0° C. Another method is the use of a cryogen spray on the patient's skin 14 for cooling down the skin 14 to a temperature of −20° C. A further method is the use of cryogen-cooled sapphire crystals that are applied to the patient's skin 14 for cooling down the skin 14 to a temperature of −10° C.

Figure 19:
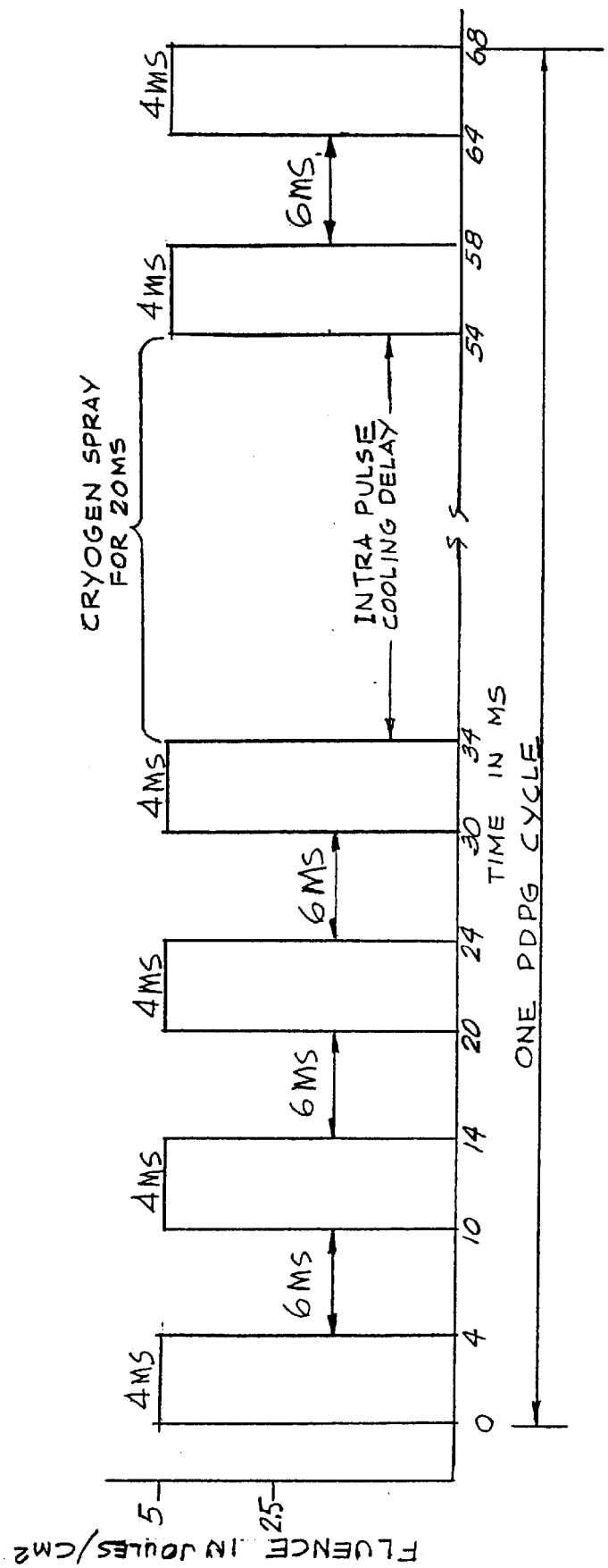
FIG. 19 is a graph showing the time profile and the optical intensity field performance for the sequential pulsing of a defined group of pulses of coherent light energy from a laser apparatus for the hair removal process and treatment of a patient demonstrating the intra-pulse cooling delay during a defined pulse group.
Figure 20:
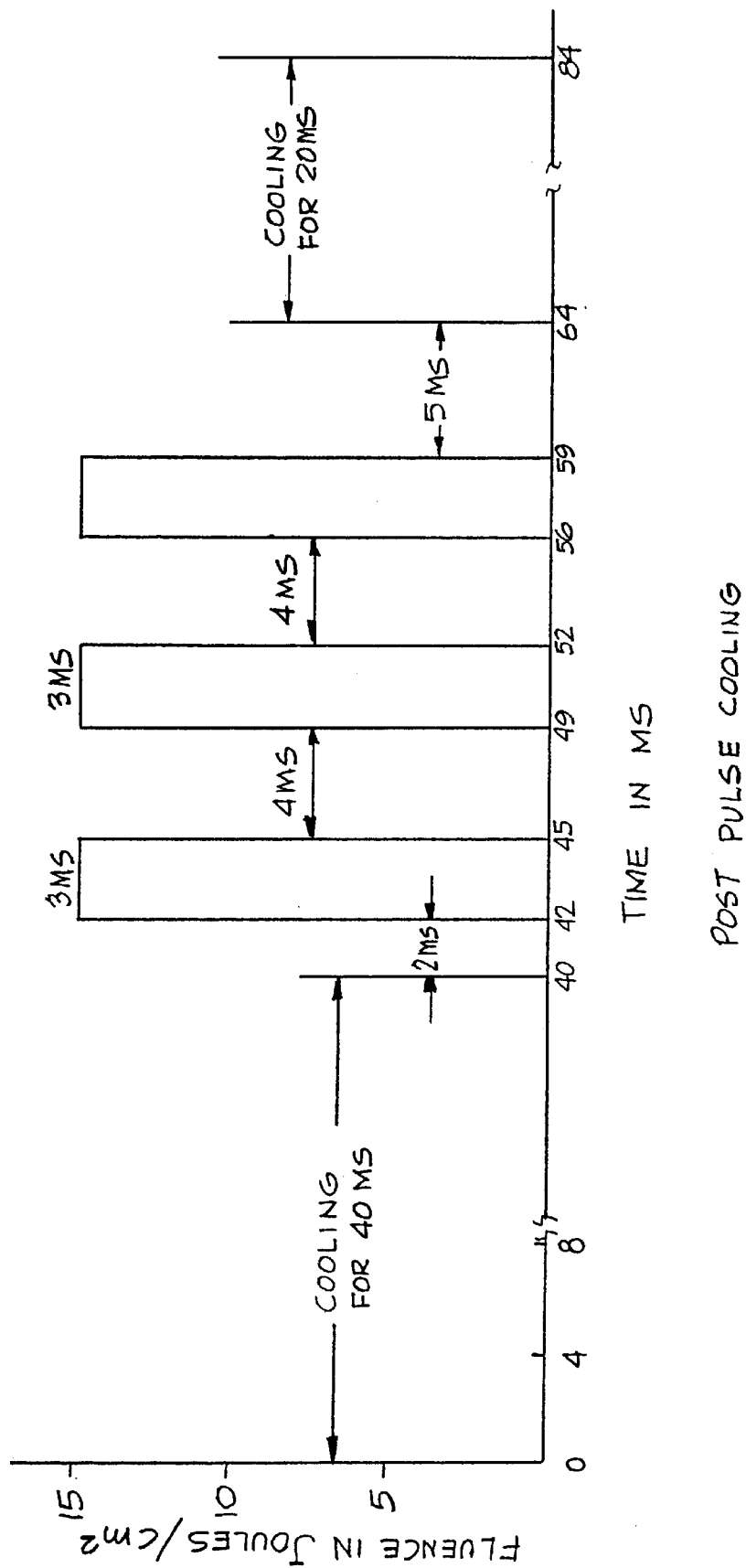
FIG. 20 is a graph showing the time profile and the optical intensity field performance for the sequential pulsing of a defined group of pulses of coherent light energy from a laser apparatus for the hair removal process and treatment of a patient demonstrating the post pulse cooling delay after a defined pulse group.

Cooling of the skin 14 (light, medium or dark colored skin) takes place during at least one delay between pulses (intra-pulse cooling) of the defined pulse group. To perform the cooling step, at least one delay between pulses is longer than the other delays between pulses in the defined pulse group. For example, as shown in FIG. 19 of the drawings, after four (4) pulses each having a duration of 4 ms, and each having a time delay of 6 ms, there is an intra-pulse cooling delay of 20 ms during which the cryogen spray is applied to the patient's skin 14. After the step of the intra-pulse cooling delay, there are two (2) more pulse durations of 4 ms with a time delay of 6 ms therebetween. This step of cooling is performed by spraying cryogen on the patient's skin 14 during the long pulse delay. The long pulse delay is in the range of 5 to 50 ms to allow time for the cooling step to be performed.

Additional cooling of the skin 14 can also be performed before and/or after emitting the defined pulse group to supplement the intra-pulse cooling step.

Alternately, the cooling step may be performed after the defined pulse group has been completed (post pulse cooling) by the optical delivery system of laser apparatus 10. This step of cooling may also performed by spraying cryogen on the patient's skin 14. The step of cooling starts within 0 to 20 ms after the completion of the defined pulse group and the spraying step has a duration of 5 to 50 ms. In the example shown in FIG. 19, a supplemental cooling step may be applied after the six (6) pulses of 4 ms duration have been applied to the patient's skin 14. This post pulse cooling step is performed after the defined pulse group is completed, and the cryogen is sprayed on the patient's skin 14 during a time period of between 5 to 50 ms.

METHOD OF THE PRESENT INVENTION

As depicted in FIG. 3, the plurality of hair shafts 12 project below the epidermis region 16 of skin area 14 and into the dermis region 18. Each hair shaft 12 extends down the follicle 20 and includes a sebaceous gland 22 and which at the anagen stage of the hair cycle further includes a follicular papilla 24 within the hair bulb 26 of hair shaft 12. The follicular papilla 24 is supplied with a plurality of small blood vessels 28 that provide the plurality of growing hair shafts 12 with nourishment. The follicular papilla 24 is an essential structure within the follicle matrix structure 30.

In order to assure destruction of the follicular papilla 24 and permanent hair removal, a sufficient laser energy level is required that does not burn the skin. In addition, the depth of penetration of the series of 74 laser beams must be sufficient to cause permanent removal of hair shaft 12 from the epidermis and dermis regions 16 and 18 of the patient's skin area 14.

Present day long pulsed single lasers operate at a maximum of 5 Herz or 5 cycles per second which allows for 200 ms between pulses. The single laser device 70 of laser apparatus 10 of the present invention allows for pulse delays of between 0.5 ms to 20 ms between pulses, and has the capability of sequentially emitting a series of 2 to 20 pulses on the same spot of the patient's skin 14.

As shown in FIGS. 1 through 3 of the drawings, the laser operator (not shown) positions the laser dispersal member 112 of the laser handpiece 110 over a selected treatment area, such as the navel area 34 of the stomach 32 of the patient being treated. The laser dispersal member 112 is positioned, as shown in FIG. 3, by the hand 36 of the laser operator such that the defined pulse group of laser pulses 74 are substantially perpendicular over the selected treatment area, such as a plurality of hair follicles 20 to be removed. Handpiece dispersal member 112 is positioned at the optimum location for directing the series of laser pulses 74 to strike the plurality of follicular papilla 24 in order to irradiate them in a proper mode. Each defined pulse group is emitted while the handpiece dispersal member 112 is stationary and maintained perpendicular to the skin. When the defined pulse group is completed, the handpiece 112 is then moved parallel to the plane of the skin and along the surface of the skin area 14 for irradiating the next area of hair follicles 20 to be removed. This is done successively, pausing the handpiece 112 while lasering and then moving the handpiece 112 between each successive defined pulse group. The handpiece 110 is then moved vertically to the next horizontal line to repeat the removal procedure. The critical regions of the hair follicle matrix structure 30 include hair follicles 20, sebaceous glands 22 and follicular papillas 24 which are irradiated such that the group of laser pulses 74 can be moved across the skin area 14 or otherwise moved over a large are of skin to be treated.

Figure 4:
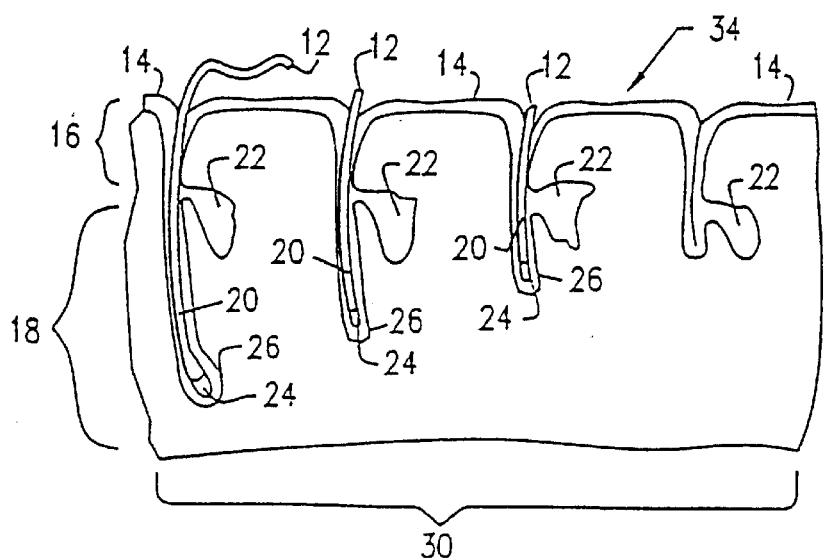
FIG. 4 is a cross-sectional view of a plurality of hair shafts within a region of skin tissue after irradiation by a laser according to the present invention and showing the gradual atrophy of the hair follicle region.

Application of the group of defined laser pulses 74 to the plurality of hair follicles 20 and to the plurality of follicular papillas 24 causes selective photothermolysis of the hair germinative apparatus, and more particularly, disruption of the hair follicle matrix structure 30 including vaporization of the deposited melanin, capillary destruction of the papillas 24, as well as vacuolation, edema, gas bubbles and protein denaturation. When the laser pulses 74 applied to the plurality of hair follicles 20 are of sufficient level, these effects will seriously injure each of the hair follicles 20 and papillas 24 being irradiated thereby permanently damaging the hair germ 26 which is responsible for hair regrowth which results in permanent hair removal. The initial laser pulse 74 of laser device 70 heats up the hair follicles 20 and subsequent laser pulses 74 supply further heat energy to vaporize the hair follicles 20, as depicted in FIGS. 3 and 4 of the drawings. This defined group of laser pulses 74 of two (2) to twenty (20) times per treatment cycle allows the hair temperature of follicles 20 to increase from room temperature of 38° C. to well over 70° C. sustained for 1 ms or longer to produce destruction of hair follicles 20.

A laser method has been provided using an improved and programmable laser apparatus by dividing the laser energy delivery into multiple, individually adjustable pulses and delivering the laser energy as a parametrically defined group of sequential pulses, with an adjustable short delay between the pulses, which allows it to achieve permanent hair removal without burning the skin on both light and dark skinned patients having either fine or coarse hair. The delay between pulses is less than the thermal relaxation time (TRT) of the hair being treated, so that the hair does not have time to dissipate its heat and cool down between pulses. This laser apparatus provides for 1) adjusting the pulse width, the number of pulses, and fluence of the laser; 2) an improved optical delivery system, so that each fired pulse is delivered to precisely the same spot; 3) the operator to precisely define the parameters of the pulse group including the delay between pulses, and adjust this delay according to clinical variables, such as skin color, hair color, and hair coarseness; and 4) the delivery of the individual pulses within each defined pulse group occurs much more rapidly than previous single long pulse lasers of the prior art, so that the delay between pulses is less than the TRT of the patient's hair 12 and skin 14. Treatment may therefore be customized according to skin color, hair color, hair diameter (hair texture being fine or coarse) and the anatomic site being treated, as described below.

The new technology requires that a series of relatively low energy laser pulses be delivered in rapid succession with short delays between pulses, to exactly the same area of the skin. Relatively low energy per pulse is delivered to the hair germinative apparatus using a series of short defined pulse groups from the laser apparatus, with the pulses repeated at short intervals so that the hair does not have time to dissipate the heat energy between pulses. For most patients, this means six pulses or less of low-energy (2 to 15 Joules/cm$^2$), short duration (2 to 6 milliseconds) pulses, separated by short delays of less than 20 milliseconds, each with a large (e.g., 10 millimeters or greater) spot size. None of the currently-produced lasers are able to produce these results. The short delay between pulses is shorter than the thermal relaxation time of the hair being treated, so the hair does not cool off between the pulses.

For example, short pulse duration lasers (with a pulse duration measured in nanoseconds) can repeat rapidly, but these are not suitable for optimal hair removal. All of the new hair removal lasers (ruby, alexandrite, diode) are long pulse lasers. Most of these recycle every 1000 milliseconds, with the fastest recycling every 100 milliseconds. The repetition rate that is necessary, however, must be a delay between pulses of less than 20 milliseconds. The new laser apparatus of the present invention is able to accomplish this new method.

The clinical circumstances which the laser operator encounters include situations where the characteristics of the laser energy delivered must be dramatically changed and parametrically defined in order to deliver enough energy without skin damage to permanently remove the hair. The reason for this is that many variables affect the way laser energy is absorbed. For instance, dark hair absorbs more laser energy than light hair, as does dark skin. Coarse hair retains the heat caused by absorption of laser energy longer than fine hair, and skin cools faster than hair. By taking advantage of these differential rates of heating and cooling one can fashion a series of laser energy pulses that will selectively and permanently remove hair.

For example, an African-American patient with dark skin and fine, black hair would need to have the energy delivered more slowly with a longer delay between pulses than a Caucasian patient. The delay between pulses is selected to be much less than the TRT of the hair. In the defined pulse group, successive pulses are emitted, each one heating the hair more, until permanent destruction of the hair is caused. The skin heats up, but not enough to cause damage. As shown by Example H of FIG. 12, the patient receives a defined pulse group of six (6) pulses of 6 milliseconds each at an energy level of 3 Joules/cm$^2$ each. The time delay is relatively long (e.g. 16 ms), and the total cycle is 116 milliseconds. Thus, 18 Joules/cm$^2$ is delivered safely to a patient to whom 18 Joules/cm$^2$ delivered in a single pulse might burn the skin.

In another example, a patient with medium (olive) skin having coarse, medium brown hair would need to have the energy delivered more slowly with a longer delay between pulses than a Caucasian patient. The delay between pulses is selected to be much less than the TRT of the hair. In the defined pulse group, successive pulses are emitted, each one heating the hair more, until permanent destruction of the hair is caused. The skin heats up, but not enough to cause damage. As shown by Example E of FIG. 9, the patient receives a defined pulse group of six (6) pulses of 4 milliseconds, each at a energy level of 4 Joules/cm$^2$ each. The time delay between pulses is relatively long (e.g. 6 ms), and the total cycle is 54 milliseconds. Thus, 24 Joules/cm$^2$ is delivered safely to a patient to whom 24 Joules/cm$^2$ delivered in a single pulse might burn the skin.

A Caucasian patient with fine, light brown hair, and light (untanned) skin requires more energy delivered in order to achieve permanent hair removal. Fine, light hair absorbs little laser energy, but even light skin will absorb some laser energy, which is why pulsed energy delivery, with a delay to allow skin cooling, allows the delivery of more laser energy, safely, to the hair germinative apparatus. In this situation, as shown by Example A of FIG. 5, the patient receives a defined pulse group of two (2) pulses of 3 milliseconds, each at a energy level of 30 Joules/cm$^2$ each. The time delay between pulses is relatively very short (e.g. 1 ms) since light skin cools faster. Thus, 60 Joules/cm$^2$ are thereby delivered safely in two (2) pulses over a 7 millisecond cycle to a patient to whom 60 Joules/cm$^2$ delivered in a single pulse might burn the skin.

Figure 5:
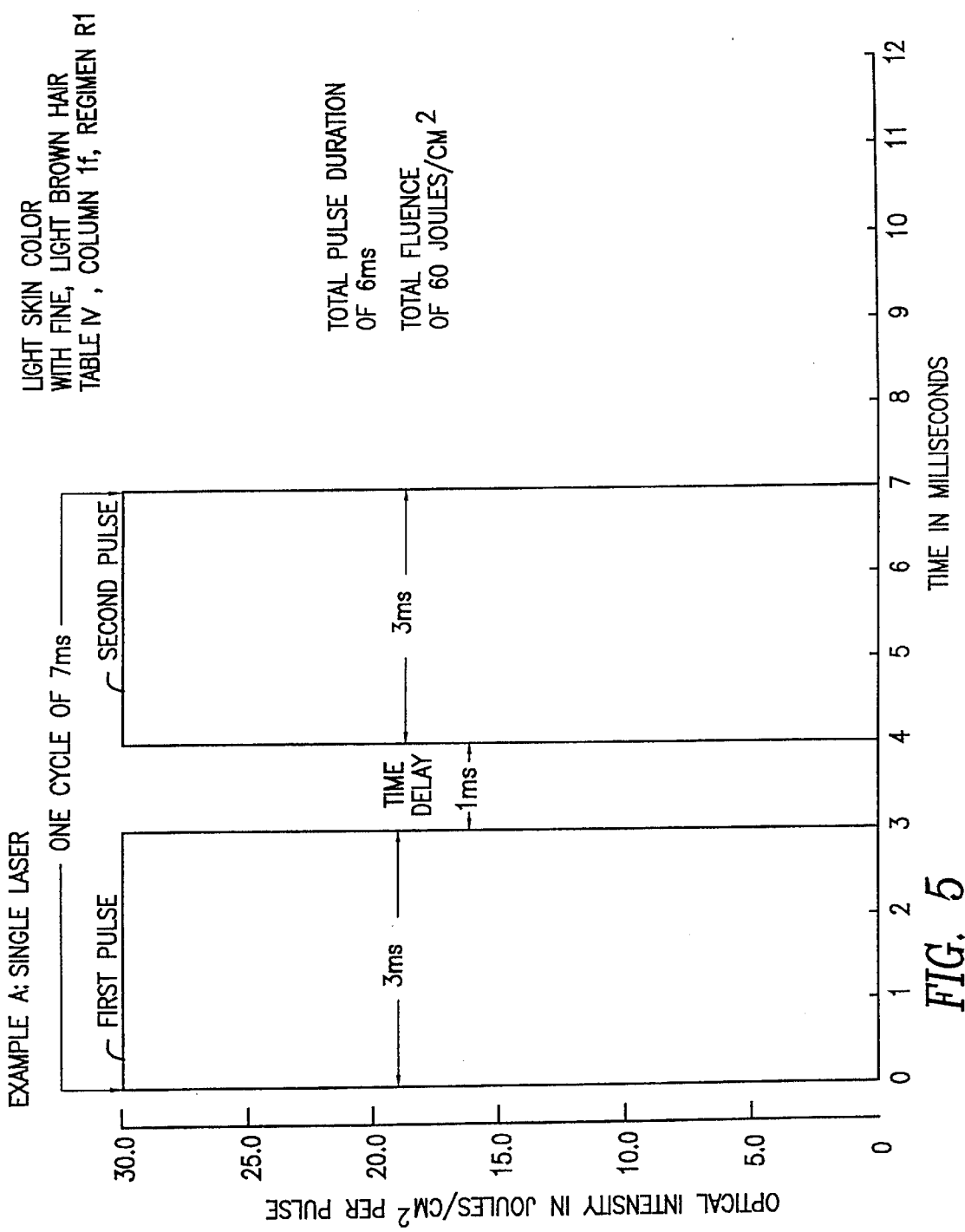
FIG. 5 is a graph showing the time profile and the optical intensity field performance for the sequential pulsing of coherent light energy of a single laser for the hair removal process and treatment of a patient having light skin color with fine, light brown hair.

The actual irradiating of the plurality of hair follicles 20 is accomplished by the laser operator depressing the pulse firing button 118 of laser handpiece 110 which in turn emits a series of laser pulses 74 in a defined pulse group over the designated treatment area 30, as shown in FIGS. 2, 3 and 5 of the drawings. A defined group of laser pulses 74 (2 to 20) of single laser device 70 are sequentially emitted for an irradiation time of 1.2 to 22 milliseconds (ms) per pulse, with a delay time between pulses of 0.5 to 20 milliseconds. The parametrically defined pulse group of sequential pulses are emitted to permanently remove the plurality of hair follicles 20 from the patient's skin area 14 being treated.

In the specific Example C for a patient with light skin color having coarse, black hair, a two (2) pulse cycle is used. As shown in detail in FIG. 7, laser 70 is controlled by sequence control device 90 so that laser 70 emits a defined pulse group having a 4 ms pulse at an energy level of 20 Joules/cm$^2$, then there is a 4 ms delay, and then laser 70 emits another 4 ms pulse at an energy level of 20 Joules/cm$^2$ to the same spot. This short delay between pulses is enough time to allow the skin being treated to slightly cool the skin 14 so that it can receive the energy (e.g. 40 Joules/cm$^2$) safely without burning the skin and permanently remove the hair in a cycle time of 12 milliseconds. In addition, the 40 Joules/cm$^2$ is enough energy to remove the hair follicles over a larger spot size (e.g. 15 mm v. 10 mm) so that a larger area of the patient can be treated in substantially less time. Spot size 75 may be circular or rectangular and a grid pattern may be used for ease of moving handpiece assembly 110 across the patient's skin 14.

The foregoing procedure is possible with the present invention because the laser apparatus (one or more lasers) is operating with a sequence control device 90 and this allows the time delay between pulses to be controlled and substantially reduced to as little as ½ of a millisecond. This short delay between the pulses is enough time to allow the skin being treated to partially cool so that it receives the energy safely without burning the skin and permanently remove the hair. Laser 70 may be pulsed in a number of different defined pulse groups to obtain the desired result.

Figure 8:
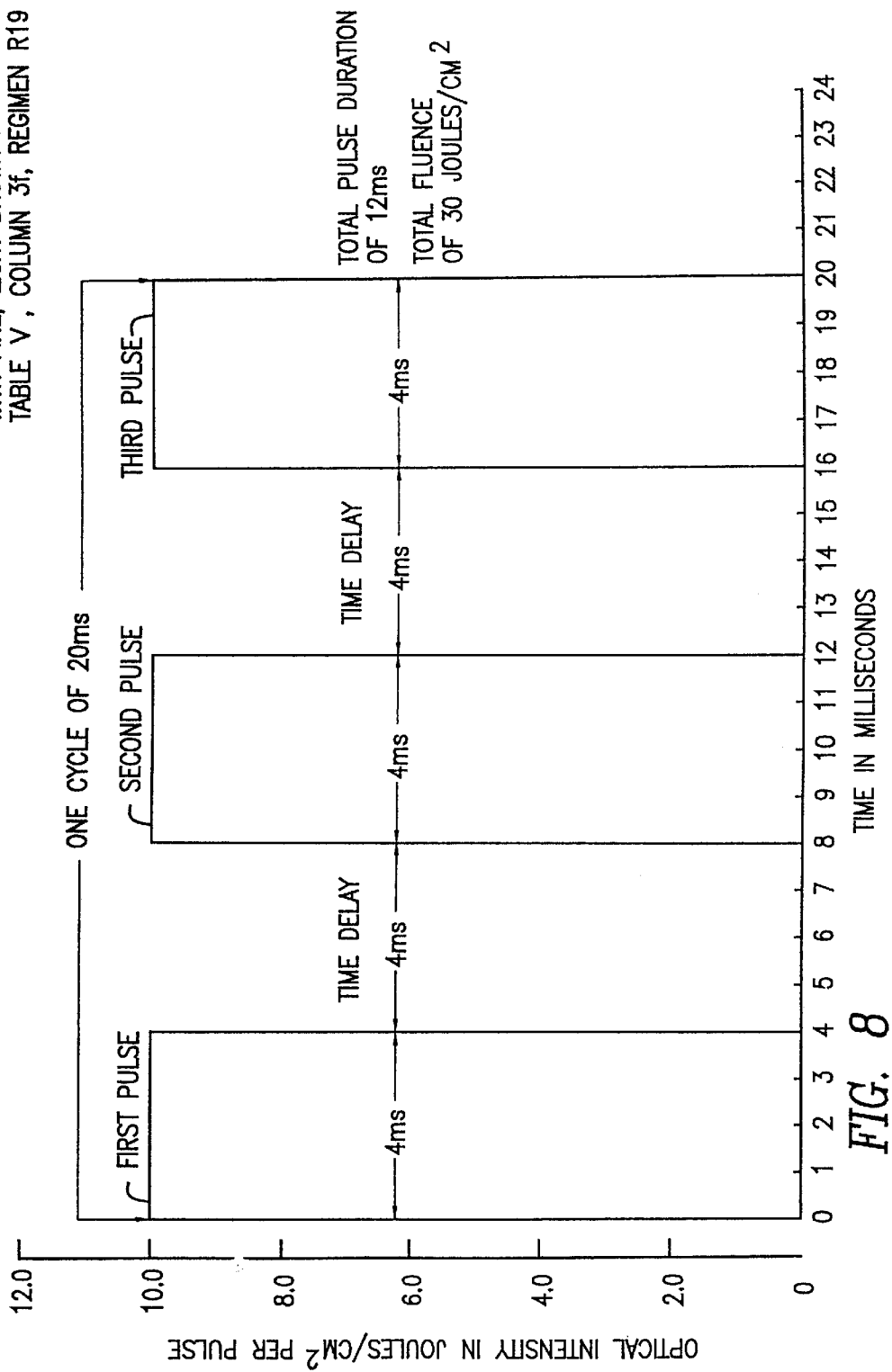
FIG. 8 is a graph showing the time profile and the optical intensity field performance for the sequential pulsing of coherent light energy of a single laser for the hair removal process and treatment of a patient having medium skin color with fine, light brown hair.
Figure 9:
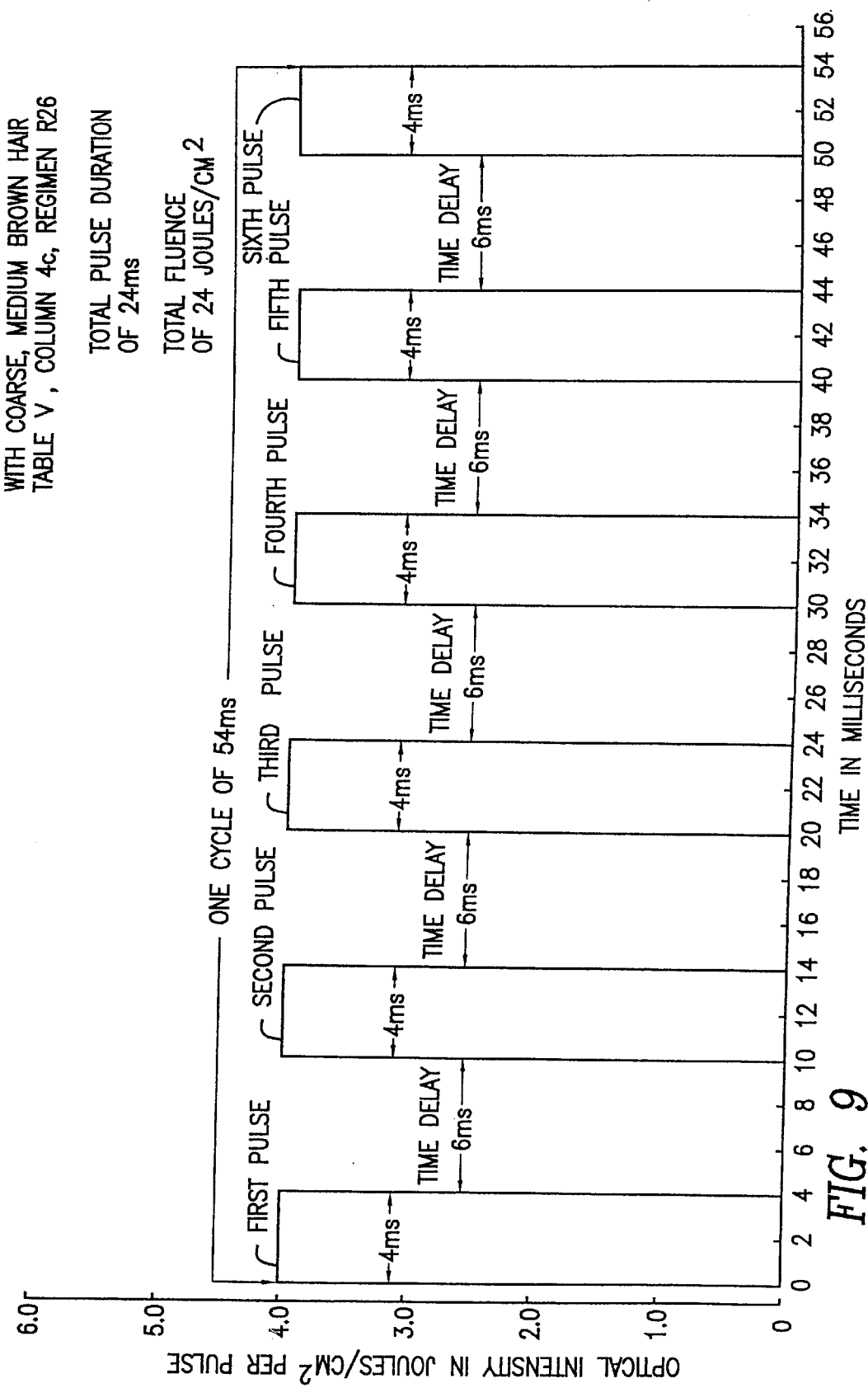
FIG. 9 is a graph showing the time profile and the optical intensity field performance for the sequential pulsing of coherent light energy of a single laser for the hair removal process and treatment of a patient having medium skin color with coarse, medium brown hair.
Figure 10:
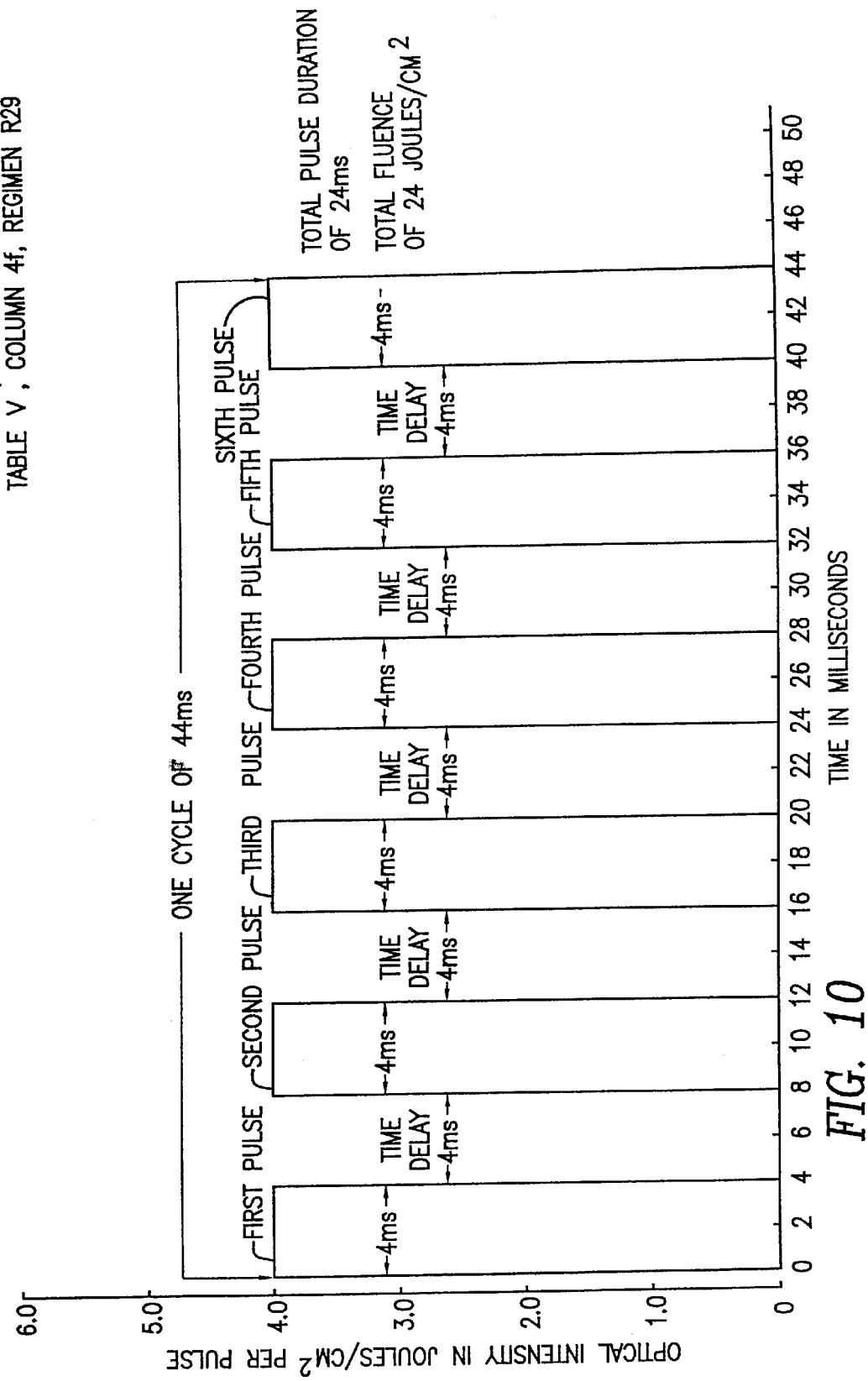
FIG. 10 is a graph showing the time profile and the optical intensity field performance for the sequential pulsing of coherent light energy of a single laser for the hair removal process and treatment of a patient having medium skin color with fine, black hair.
Figure 11:
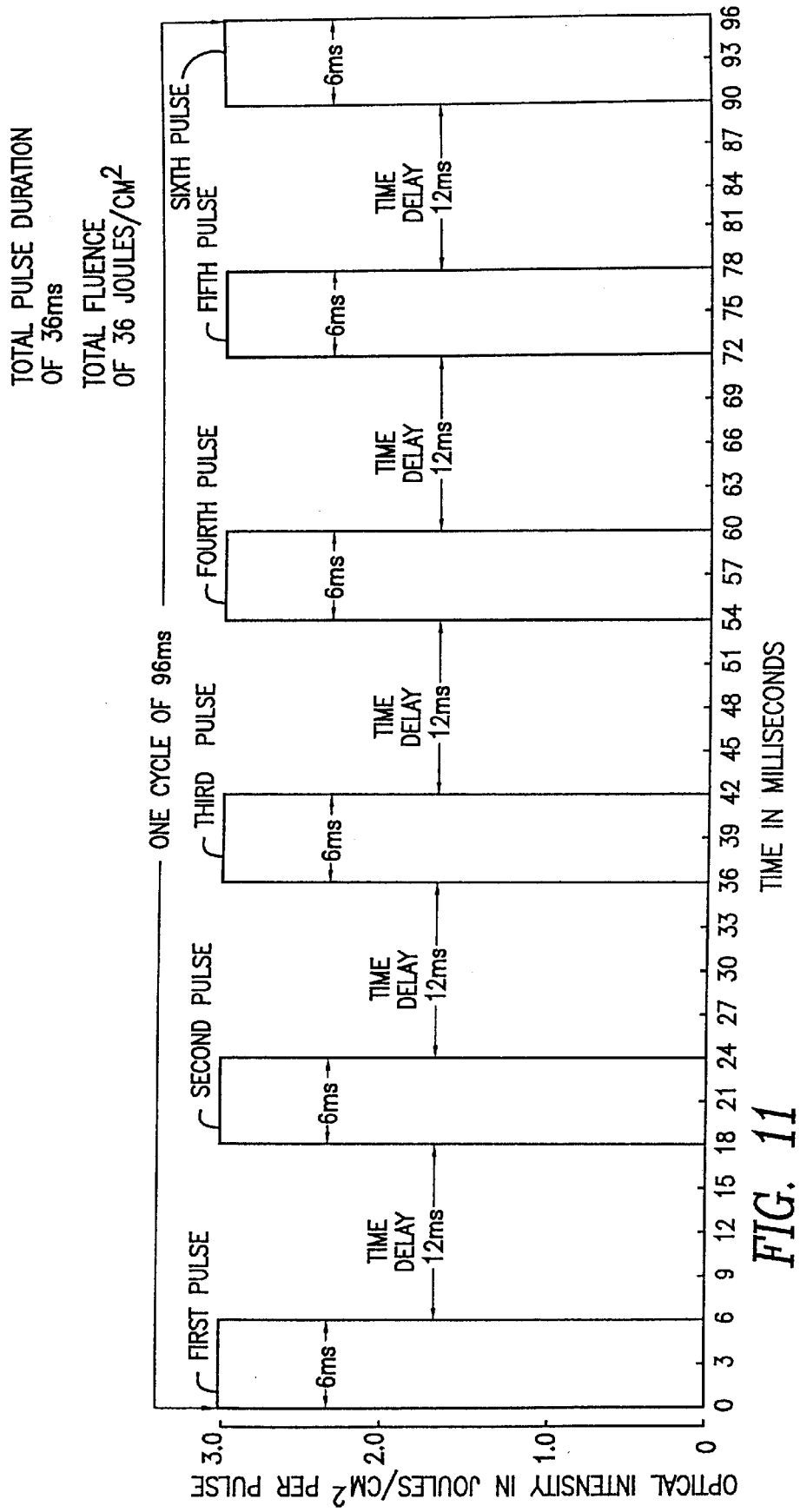
FIG. 11 is a graph showing the time profile and the optical intensity field performance for the sequential pulsing of coherent light energy of a single laser for the hair removal process and treatment of a patient having dark skin color with coarse, medium brown hair.
Figure 12:
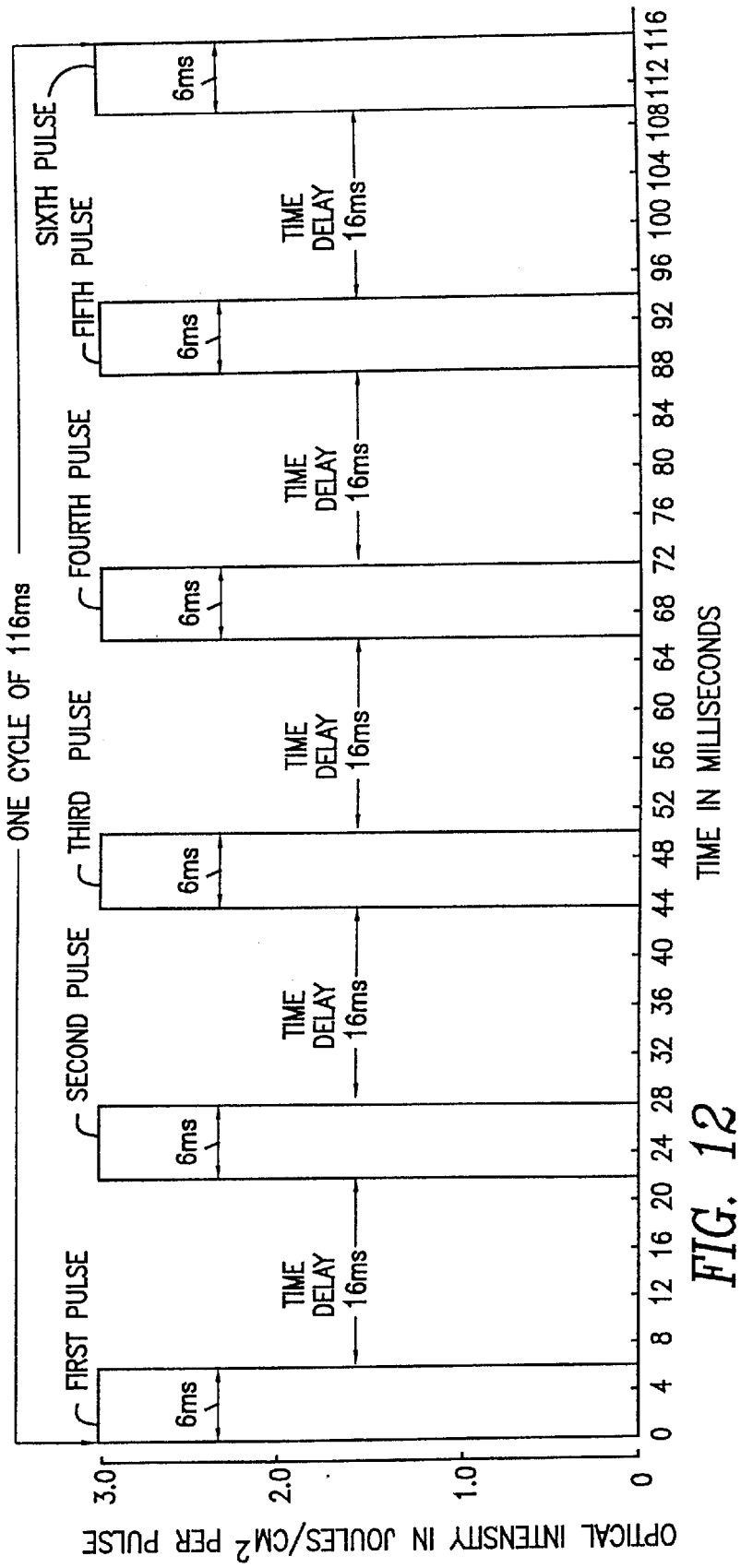
FIG. 12 is a graph showing the time profile and the optical intensity field performance for the sequential pulsing of coherent light energy of a single laser for the hair removal process and treatment of a patient having dark skin color with fine, black hair.

Another example of a treatment cycle is a medium skin color patient (e.g. Hispanic) with fine, light brown hair, as shown in Example D of FIG. 8. For permanently removing hair follicles 20 using a single laser 70 the laser is programmed to emit a defined pulse group of pulses 74 at an energy level of 10 Joules/cm$^2$ per pulse with an irradiation pulse duration of 4 ms per pulse for a series of three (3) pulses, and the time delay between each of the 3 pulses is 4 ms. The complete treatment cycle of the defined group includes pulsed irradiation time (3×4 ms) of 12 ms plus two (2) time delays (2×4 ms) of 8 ms for a total treatment cycle time (12 ms+8 ms) of 20 ms at a total energy level of 30 Joules/$^2$ (3 pulses×10 Joules/cm$^2$ per pulse). This treatment cycle is sufficient to safely and permanently remove the plurality of hair follicles 20 being treated by laser pulses 74 of the laser apparatus 10, as shown in FIGS. 3 and 8 of the drawings.

Figure 13:
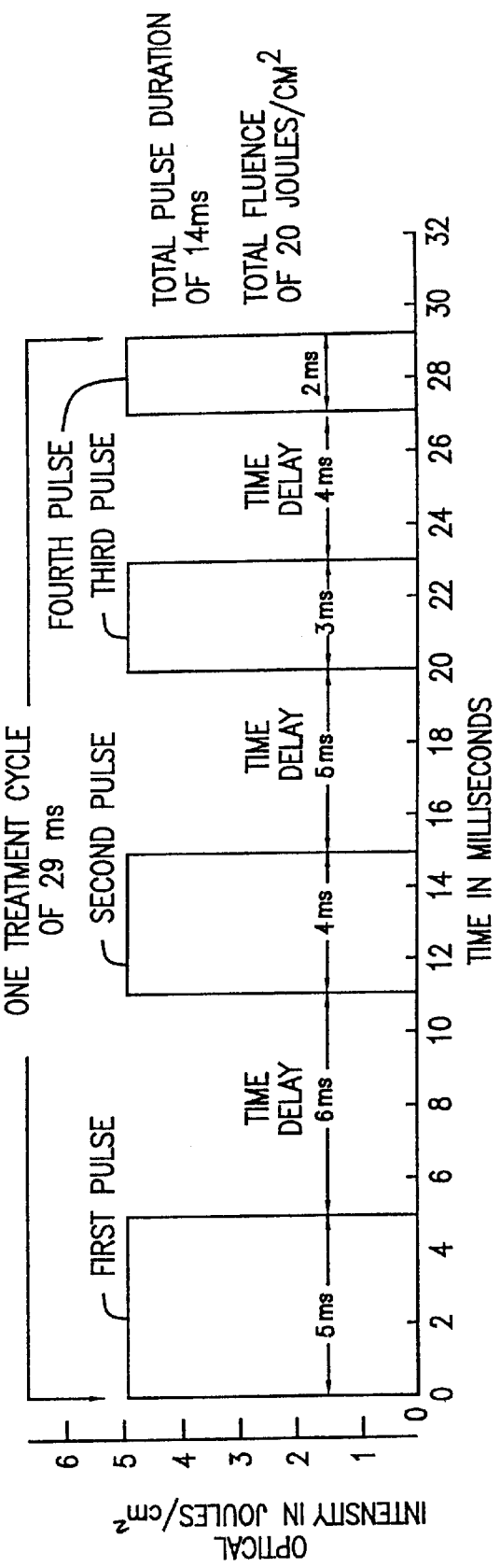
FIG. 13 is a graph showing the time profile and the optical intensity field performance for the sequential pulsing of coherent light energy of a single laser varying both duration of pulses and delay times between pulse for the hair removal process and treatment of a patient having dark skin color with fine, black hair, when active selective epidermal cooling is used. Note that shorter delays and higher total fluence may be used.
Figure 14:
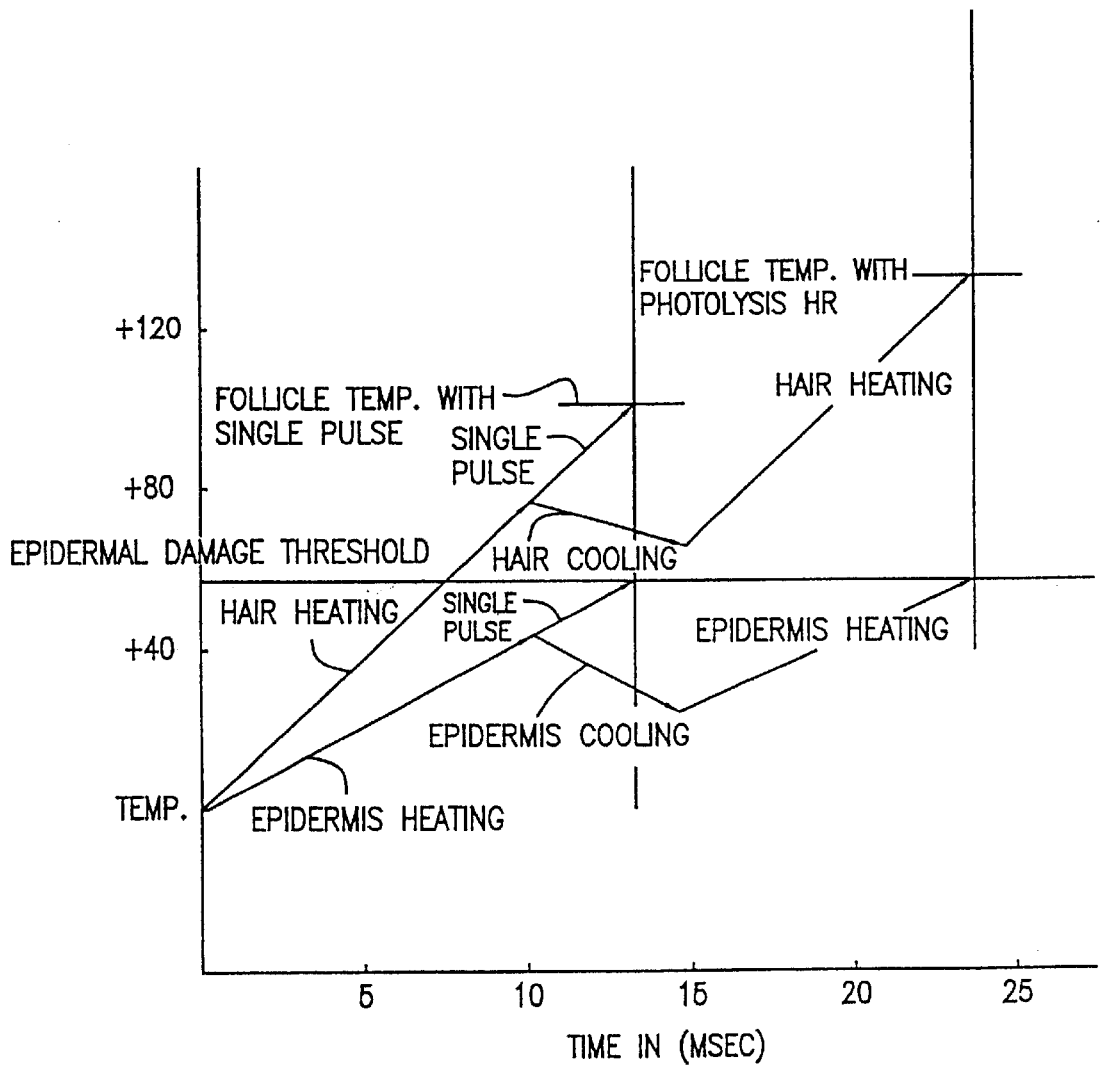
FIG. 14 is a graph showing the multipulsing of the single laser (with appropriate tuning with respect to power level, pulse width, time delay between pulses, etc.) for optimization of the epidermal damage threshold with respect to time and temperature.

In another example, as depicted in Example I of FIG. 13, the laser operator may operate laser device 70 to emit a defined pulse group having pulses at different pulse durations of 5 ms, 4 ms, 3 ms and 2 ms with different delay times of 6 ms, 5 ms and 4 ms between the pulses, at an energy level of 5 Joules/cm$^2$ per pulse, with a laser beam diameter 75 of 15 millimeters. For a specific treatment cycle, the operator programs the above treatment parameters into the programmable control panel 120, as shown in FIG. 13 of the drawings, in the following manner. The laser operator initiates the programming of the specific treatment cycle by turning ON the control panel 120 via ON/OFF button 122. The operator then selects and activates the control knob 124 for adjusting the power level to 5 Joules/cm$^2$ for laser device 70, and then the operator keys in the 5 Joules/cm$^2$ via keyboard 134 for each of the pulses of 5 ms, 4 ms, 3 ms and 2 ms and this data is then visually displayed on display screen 132. If the power level for each pulse duration is correct the operator presses the "ENTER" key on keyboard 134 in order to enter the data in control panel 120. Next, the laser operator then selects and activates the control knob 130 for adjusting the laser beam diameter 75 of laser device 70 to be a 15 millimeter diameter.

Then the operator keys in the 15 millimeters for laser beam diameter 75 via keyboard 134 for each of the pulses of 5 ms, 4 ms, 3 ms and 2 ms, and this data is then visually displayed on display screen 132. If the laser beam diameter 75 for each pulse duration is correct the operator presses the "ENTER" key on keyboard 134 in order to enter this data in control panel 120. The next step of programming by the laser operator is the selection and activation of the control knob 126 for pulse duration of laser 70, at which time the operator then keys in the aforementioned data/information via keyboard 134 so that the first pulse duration is 5 ms, the second pulse duration is 4 ms, the third pulse duration is 3 ms, and the fourth pulse is 2 ms, and it is then visually displayed on display screen 132. If the series of pulse durations are correct the operator presses the "ENTER" key on keyboard 134 to enter the above data into the programmable control panel 120. The last step of programming by the laser operator is the selection and activation of the control knob 128 for pulse delay time between irradiation pulses of laser device 70, at which time the operator then keys in the aforementioned information via keyboard 134 so that the first pulse delay time of 6 ms is between the pulses of 5 ms and 4 ms, the second delay time of 5 ms is between the pulses of 4 ms and 3 ms, and the third delay time of 4 ms is between the pulses of 3 ms and 2 ms, and it is then visually displayed on display screen 132. If the series of time delays between pulses are correct, the operator presses the "ENTER" key on keyboard 134 to enter the above information/data in the programmable control panel 120.

Laser apparatus 10 is now ready to fire the parametrically defined group of laser pulses 74 as programmed. Laser operator depresses the pulse firing button 118 over the selected treatment area 34 to start the pulsed treatment cycle. There is a first pulse irradiation time of 5 ms followed by a first time delay of 6 ms, sequentially followed by a second pulse irradiation time of 4 ms followed by a second time delay of 5 ms, sequentially followed by a third pulse irradiation time of 3 ms and third time delay of 4 ms, and sequentially followed by a fourth pulse irradiation time of 2 ms. The complete treatment cycle of pulsed irradiation and delay times is thus 29 milliseconds at a total energy level of 20 Joules/cm$^2$ (four (4) pulses at 5 Joules/cm$^2$ per pulse) which is sufficient to permanently remove the plurality of hair follicles 20 of the patient's skin area 14 being treated by laser beams 74 of laser apparatus 10, as shown in FIG. 3 of the drawings, for a patient having dark skin color, with coarse, medium brown hair. Immediately prior to, and/or during laser firing, there is active epidermal cooling using a cryogen spray or similar device, as explained above.

Alternatively, the articulated laser arm assembly 222 with laser dispersal member 228 and pulse firing button 226, as shown in FIG. 1A, is operated in a similar manner as in the preferred embodiment described above. Other optical delivery systems, such as a light path or pipe for a diode laser, may be used to deliver laser energy to the skin without requiring use of a fiber optic delivery system.

As shown in FIG. 4, the laser-damaged follicles 20 will gradually recede due to destruction of the follicle matrix structure 30, including disruption of blood flow from the blood vessel capillaries 28 to each of the papillas 24. The hair follicles 20 show gradual atrophy without a blood supply thereby causing permanent hair removal.

Different types of hair and skin pigmentation, different cooling times of the epidermis, and hair follicles of different sizes, as well as the location of body hair to be removed will require different methods of laser treatment to fit the individual needs of the patient undergoing the therapeutic laser treatment for permanent hair removal. This laser treatment of parametrically defined groups of laser pulses 74 allows the laser operator to individually adjust each of the parameters of energy/power level, pulse width duration, number of pulses, pulse delay and laser beam diameter 75 for the particular patient by using control panel 120 which controls the single laser device 70 of laser apparatus 10 of the present invention.

EXAMPLES OF THE PRESENT INVENTION

Based on the Tables V, VI and VII, as depicted in the specification, the method of the present invention demonstrates 35 different treatment regimens that are based on the skin color (being light skin, medium skin and dark skin), on the hair color (being light brown hair, medium brown hair and black hair), and on the type of hair texture (being fine or coarse). Each treatment regimen, as shown in Tables IV, V and VI, includes the following parameters:

1) the total fluence in Joules/cm$^2$,
2) the number of pulses,
3) the pulse width in milliseconds for each pulse,
4) the pulse delay in milliseconds for each time delay,
5) the fluence (power level) per pulse in Joules/cm$^2$, and
6) the energy rate in Joules/cm$^2$ ms.

The laser apparatus 10 is designed and operated such that the laser operator can easily and quickly vary the following four laser parameters of: 1) fluence (power level) per pulse, 2) pulse width/duration per pulse, 3) pulse time delay between pulses, and 4) the number of pulses per treatment regimen. These four parameters can be changed individually or in any combination at the patient's bedside while conducting the treatment regimen. These parameters must fall within the ranges, as specified in each of the Tables I, II, III and IV as shown in the specification, and must be sufficiently variable within the ranges, so as to allow the laser operator to optimize the treatment regimen based on skin color, hair color and hair texture (diameter). The values given are for use when epidermal cooling is accomplished using optically translucent (clear) ultrasound gel cooled to between 2 to 5° C., or the direct application of ice to the epidermis immediately prior to laser pulsing. More effective active epidermal cooling will allow the use of higher total fluence and shorter delays between pulses. (Not including, of course, the one longer delay needed if intrapulse cooling is used). These other methods of active selective epidermal cooling include the use of a cryogen sprayed on the epidermis or a cooled optically translucent contact applicator, either used immediately prior to, and/or during, and/or after the laser emission.

TABLE I

SUMMARY OF PARAMETERS FOR EACH SKIN COLOR, ALL HAIR COLORS AND HAIR TEXTURES USING A LASER APPARATUS PARAMETERS

| | | | |
|---|---|---|---|
| SKIN COLOR | LIGHT SKIN | MEDIUM SKIN | DARK SKIN |
| HAIR COLOR | LIGHT BROWN HAIR MEDIUM BROWN HAIR BLACK HAIR | LIGHT BROWN HAIR MEDIUM BROWN HAIR BLACK HAIR | MEDIUM BROWN HAIR BLACK HAIR |
| HAIR TEXTURE | 1 f to 2.5 c | 3 f to 4 c | 5 f to 6 c |
| Total Fluence in Joules/cm$^2$ | 4 to 100 | 4 to 50 | 4 to 50 |
| Number of Pulses | 2 to 10 | 2 to 12 | 2 to 15 |
| Pulse Width in milliseconds | 1.2 to 10 | 1.5 to 10 | 1.5 to 22 |
| Pulse Delay in milliseconds | 0.5 to 6 | 1 to 6 | 2 to 20 |
| Total Pulse Duration in milliseconds | 2.4 to 60 | 3.0 to 120 | 3.0 to 330 |
| Power Level per Pulse in Joules/cm$^2$ | 2 to 35 | 2 to 15 | 1.5 to 10 |
| Wavelength in nanometers | 550 to 1200 | 550 to 1200 | 550 to 1200 |
| Beam Diameter in millimeters | 4 to 50 | 4 to 50 | 4 to 50 |

TABLE II

LIGHT SKIN COLOR USING A LASER APPARATUS PARAMETERS

| HAIR COLOR HAIR TEXTURE | ALL HAIR COLORS 1 f to 2.5 c | LIGHT BROWN HAIR 1 f to 2.5 f | LIGHT BROWN HAIR 1 c to 2.5 c | MEDIUM BROWN HAIR 1 f to 2.5 f | MEDIUM BROWN HAIR 1 c to 2.5 c | BLACK HAIR 1 f to 2.5 f | BLACK HAIR 1 c to 2.5 c |
|---|---|---|---|---|---|---|---|
| Total Fluence in Joules/cm$^2$ | 4 to 100 | 40 to 100 | 40 to 100 | 40 to 100 | 40 to 100 | 40 to 100 | 30 to 100 |
| Number of Pulses | 2 to 10 | 2 to 4 | 2 to 4 | 2 to 4 | 2 to 6 | 2 to 6 | 2 to 10 |
| Pulse Width in milliseconds | 1.2 to 10 | 1.2 to 4 | 1.2 to 4 | 1.5 to 4 | 1.5 to 4 | 1.5 to 4 | 2 to 6 |
| Pulse Delay in milliseconds | 0.5 to 6 | 0.5 to 2 | 1 to 2 | 1 to 2 | 2 to 4 | 1 to 3 | 2 to 4 |

TABLE III

MEDIUM SKIN COLOR USING A LASER APPARATUS PARAMETERS

| HAIR COLOR HAIR TEXTURE | ALL HAIR COLORS 3 f to 4 c | LIGHT BROWN HAIR 3 f & 4 f | LIGHT BROWN HAIR 3 c & 4 c | MEDIUM BROWN HAIR 3 f & 4 f | MEDIUM BROWN HAIR 3 c & 4 | BLACK HAIR 3 f & 4 f | BLACK HAIR 3 c & 4 c |
|---|---|---|---|---|---|---|---|
| Total Fluence in Joules/cm$^2$ | 20 to 50 | 30 to 50 | 30 to 50 | 30 to 50 | 30 to 50 | 24 to 50 | 20 to 50 |
| Number of Pulses | 2 to 12 | 3 to 6 | 3 to 8 | 3 to 8 | 3 to 8 | 3 to 10 | 3 to 12 |
| Pulse Width in milliseconds | 1.5 to 10 | 1.5 to 4 | 1.5 to 4 | 1.5 to 4 | 2 to 5 | 2 to 5 | 4 to 6 |
| Pulse Delay in milliseconds | 1 to 6 | 1 to 4 | 3 to 6 | 2 to 5 | 4 to 6 | 2 to 5 | 4 to 6 |

TABLE IV

DARK SKIN COLOR USING A LASER APPARATUS PARAMETERS

| HAIR COLOR HAIR TEXTURE | ALL HAIR COLORS 5 f to 6 c | MEDIUM BROWN HAIR 5 c & 6 c | BLACK HAIR 5 f & 6 f | BLACK HAIR 5 c & 6 c |
|---|---|---|---|---|
| Total Fluence in Joules/cm$^2$ | 4 to 50 | 18 to 40 | 18 to 40 | 15 to 40 |
| Number of Pulses | 2 to 15 | 4 to 8 | 2 to 10 | 4 to 15 |

TABLE IV-continued

DARK SKIN COLOR USING A LASER APPARATUS
PARAMETERS

| HAIR COLOR<br>HAIR TEXTURE | ALL HAIR COLORS<br>5 f to 6 c | MEDIUM BROWN HAIR<br>5 c & 6 c | BLACK HAIR<br>5 f & 6 f | BLACK HAIR<br>5 c & 6 c |
|---|---|---|---|---|
| Pulse Width in milliseconds | 1.5 to 22 | 4 to 10 | 4 to 12 | 5 to 22 |
| Pulse Delay in milliseconds | 2 to 20 | 2 to 14 | 4 to 16 | 6 to 20 |

TABLE V

LIGHT SKIN COLOR USING A LASER APPARATUS

| PARAMETERS | 1 f | 1 c | 2 f | 2 c | 2.5 f | 2.5 c |
|---|---|---|---|---|---|---|
| A. LIGHT BROWN HAIR COLOR | R1 | R2 | R3 | R4 | R5 | R6 |
| Total Fluence in Joules/cm$^2$ | 60 | 60 | 50 | 50 | 40 | 40 |
| Number of Pulses | 2 | 2 | 2 | 2 | 2 | 2 |
| Pulse Width in milliseconds | 3 | 3 | 3 | 3 | 4 | 4 |
| Pulse Delay in milliseconds | 1 | 2 | 2 | 4 | 2 | 4 |
| Total Pulse Duration in ms | 6 | 6 | 6 | 6 | 8 | 8 |
| Fluence per Pulse in Joules/cm$^2$ | 30 | 30 | 25 | 25 | 20 | 20 |
| Energy Rate in Joules/cm$^2 \cdot$ ms | 10 | 10 | 8⅓ | 8⅓ | 5 | 5 |
| B. MEDIUM BROWN HAIR COLOR | R7 | R8 | R9 | R10 | R11 | R12 |
| Total Fluence in Joules/cm$^2$ | 60 | 60 | 50 | 50 | 40 | 40 |
| Number of Pulses | 2 | 2 | 2 | 2 | 2 | 2 |
| Pulse Width in milliseconds | 3 | 3 | 3 | 3 | 4 | 4 |
| Pulse Delay in milliseconds | 1 | 2 | 2 | 4 | 2 | 4 |
| Total Pulse Duration in ms | 6 | 6 | 6 | 6 | 8 | 8 |
| Fluence per Pulse in Joules/cm$^2$ | 30 | 30 | 25 | 25 | 20 | 20 |
| Energy Rate in Joules/cm$^2 \cdot$ ms | 10 | 10 | 8⅓ | 8⅓ | 5 | 5 |
| C. BLACK HAIR COLOR | R13 | R14 | R15 | R16 | R17 | R18 |
| Total Fluence in Joules/cm$^2$ | 50 | 50 | 50 | 50 | 40 | 40 |
| Number of Pulses | 2 | 2 | 2 | 2 | 2 | 2 |
| Pulse Width in milliseconds | 3 | 3 | 3 | 3 | 4 | 4 |
| Pulse Delay in milliseconds | 2 | 3 | 2 | 4 | 2 | 4 |
| Total Pulse Duration in ms | 6 | 6 | 6 | 6 | 8 | 8 |
| Fluence per Pulse in Joules/cm$^2$ | 25 | 25 | 25 | 25 | 20 | 20 |
| Energy Rate in Joules/cm$^2 \cdot$ ms | 8⅓ | 8⅓ | 8⅓ | 8⅓ | 5 | 5 |

TABLE VI

MEDIUM SKIN COLOR USING A LASER APPARATUS

| PARAMETERS | 3 f | 3 c | 4 f | 4 c |
|---|---|---|---|---|
| A. LIGHT BROWN HAIR COLOR | R19 | R20 | R21 | R22 |
| Total Fluence in Joules/cm$^2$ | 30 | 30 | 24 | 24 |
| Number of Pulses | 3 | 3 | 6 | 6 |
| Pulse Width in milliseconds | 4 | 4 | 4 | 4 |
| Pulse Delay in milliseconds | 4 | 6 | 4 | 6 |
| Total Pulse Duration in ms | 12 | 12 | 24 | 24 |
| Fluence per Pulse in Joules/cm$^2$ | 10 | 10 | 4 | 4 |
| Energy Rate in Joules/cm$^2 \cdot$ ms | 2.5 | 2.5 | 1 | 1 |
| B. MEDIUM BROWN HAIR COLOR | R23 | R24 | R25 | R26 |
| Total Fluence in Joules/cm$^2$ | 30 | 30 | 24 | 24 |
| Number of Pulses | 3 | 3 | 6 | 6 |
| Pulse Width in milliseconds | 4 | 4 | 4 | 4 |
| Pulse Delay in milliseconds | 4 | 6 | 4 | 6 |
| Total Pulse Duration in ms | 12 | 12 | 24 | 24 |
| Fluence per Pulse in Joules/cm$^2$ | 10 | 10 | 4 | 4 |
| Energy Rate in Joules/cm$^2 \cdot$ ms | 2.5 | 2.5 | 1 | 1 |
| C. BLACK HAIR COLOR | R27 | R28 | R29 | R30 |
| Total Fluence in Joules/cm$^2$ | 30 | 30 | 24 | 24 |
| Number of Pulses | 3 | 3 | 6 | 6 |
| Pulse Width in milliseconds | 4 | 4 | 4 | 4 |
| Pulse Delay in milliseconds | 4 | 6 | 4 | 6 |
| Total Pulse Duration in ms | 12 | 12 | 24 | 24 |
| Fluence per Pulse in Joules/cm$^2$ | 10 | 10 | 4 | 4 |
| Energy Rate in Joules/cm$^2 \cdot$ ms | 2.5 | 2.5 | 1 | 1 |

TABLE VII

DARK SKIN COLOR USING A LASER APPARATUS

| PARAMETERS | 5 f | 5 c | 6 f | 6 c |
|---|---|---|---|---|
| A. LIGHT BROWN HAIR COLOR | NA | NA | NA | NA |
| Total Fluence in Joules/cm$^2$ | | | | |
| Number of Pulses | | | | |
| Pulse Width in milliseconds | | | | |
| Pulse Delay in milliseconds | | | | |
| Total Pulse Duration in ms | | | | |
| Fluence per Pulse in Joules/cm$^2$ | | | | |
| Energy Rate in Joules/cm$^2$ | | | | |
| B. MEDIUM BROWN HAIR COLOR | NA | R31 | NA | NA |
| Total Fluence in Joules/cm$^2$ | | 18 | | |
| Number of Pulses | | 6 | | |
| Pulse Width in milliseconds | | 6 | | |
| Pulse Delay in milliseconds | | 12 | | |
| Total Pulse Duration in ms | | 36 | | |
| Fluence per Pulse in Joules/cm$^2$ | | 3 | | |
| Energy Rate in Joules/cm$^2 \cdot$ ms | | 0.5 | | |
| C. BLACK HAIR COLOR | R32 | R33 | R34 | R35 |
| Total Fluence in Joules/cm$^2$ | 18 | 18 | 18 | 18 |
| Number of Pulses | 6 | 6 | 6 | 6 |
| Pulse Width in milliseconds | 5 | 5 | 6 | 6 |
| Pulse Delay in milliseconds | 12 | 14 | 16 | 20 |
| Total Pulse Duration in ms | 30 | 30 | 36 | 36 |
| Fluence per Pulse in Joules/cm$^2$ | 3 | 3 | 3 | 3 |
| Energy Rate in Joules/cm$^2 \cdot$ ms | 0.6 | 0.6 | 0.5 | 0.5 |

The essential elements to these various treatment regimens based upon the method of operation of the present invention demonstrates that the laser apparatus can deliver finely tuned defined pulse groups as defined in Tables V, VI and VII. The operator can provide proper adjustment of this laser apparatus 10 to fit the individual clinical parameters and response of the patient. This adjustment is a summarization based on the observed response of the patient's skin and hair to the test laser pulses in order to determine the final laser parameters which are selected for treatment.

Both of the above elements of parametrically defined pulse groups and final laser parameters based upon the patients' needs are necessary because of the fine adjustment needed to achieve success with safety. The margin of error has been estimated to be on the order of 2%, i.e. 2% lower than the optimal setting leads to failure to achieve epilation, and 2% higher leads to epidermal damage.

The selection of these final laser parameters to be used on a given patient is done in two basic steps: the first step is an estimate which is made of the starting parameters to be used (see Tables I, II, III and IV); and the second step is a series of test pulses that are administered to a small area on the patient and the above parameters are then adjusted based on the actual and carefully observed response of the patient's skin and hair to the test pulses administered. A final setting is then selected from one of the specific regimens R1 to R35 in Tables IV, V and VI which is used to treat the larger remaining area for which epilation is desired.

The pre-set combination of the above four laser parameters is chosen according to the patient's skin color (types 1, 2, 2½, 3, 4, 5 and 6), the color of the hair being treated (blonde, red, light brown, dark brown, or black), and the diameter of the hair being treated (fine or coarse). Consideration is given to other factors influencing skin color, particularly beta-carotene and recent tanning, and the anatomic area being treated (a large area, such as the back, is treated less aggressively than a small area, such as a sideburn). Ethnicity is also carefully considered, with caution being used for African-American, Asian, Middle Eastern, and other dark skinned peoples.

For a given patient the method works as follows: A matrix is consulted which contains pre-set combinations of the four laser parameters. For any given combination of skin color, hair color, and hair diameter (as detailed above) one pre-set combination is found in the matrix of 35 regimens R1 to R35. Each regimen specifies each of the four laser parameters to be set, as shown in Tables V, VI and VII. Using this pre-set combination a test pulse is administered to the patient. The object is to vaporize the hair without adversely affecting the skin. This normally requires using the maximum energy tolerated by the skin. The response of the patient's skin to the test pulse is carefully observed both immediately and for several minutes following the test pulse. The parameters are then readjusted as shown in the following steps:

1. If the skin does not become pink the fluence (power level) is increased; if the skin is too red the fluence is decreased.
2. Dark skin requires any or all of the following: decreased fluence, increased number of pulses, increased delay between pulses, or increased pulse duration.
3. Fine hair requires the opposite of step #2, i.e. any or all of the following: increased fluence, decreased number of pulses, decreased delay between pulses, or decreased pulse duration.
4. Light hair requires the same as step #3.
5. Dark hair can be treated with the same as step #2.
6. Too much skin reaction (too red) requires the same as step #2.
7. When adjusting the above parameters small increments are made. For example, if increasing the pulse delay, it is by only one or two milliseconds at a time.
8. Fine adjustment and observation will yield the optimal combination of the four laser parameters which produces effective laser hair removal without adverse effects on the skin.

Examples A to I represent 8 of the 35 treatment regimens (R1 to R35) of Tables V, VI and VII based on various types of skin color, hair color and hair texture (diameter). In each of the Examples A to I the parameters shown by each of the graphs include number of pulses, pulse width in milliseconds, pulse time delay in milliseconds, fluence (power level) per pulse in Joules/cm$^2$, and a one cycle treatment time in milliseconds. In addition, a total pulse duration in milliseconds and a total fluence (power level) in Joules/cm$^2$ are indicated on each graph.

The principles on which the multipulsed laser apparatus 10 of the present invention is used include the following elements:

1. Hair removal is effective only when the hair to be treated is darker than the skin, and in this circumstance the hair heats faster and cools slower than the skin.
2. Parametrically defined pulse groups with the appropriate selected parameters (energy fluence/power level, number of pulses, pulse width, delay between pulses, etc.) allows one to achieve greater efficacy with greater safety (see FIG. 14 of graph A).
3. As skin color darkens the operator must deliver less energy more slowly when treating the patient.
4. Coarse hair can be treated with greater delays between pulses because the thermal relaxation time is longer.
5. Light hair requires greater energy fluence and shorter delays between pulses.
6. To deliver energy more slowly the operator can increase the number of pulses, increase the duration of each pulse, or increase the delay between pulses when treating the patient.

ADVANTAGES OF THE PRESENT INVENTION

Accordingly, an advantage of the present invention is that it provides an improved laser apparatus and method which supplies a defined pulse group of laser pulses with short delays between the pulses from a laser apparatus to heat a hair follicle and hair follicle shaft to cause permanent damage to that hair follicle and shaft, and yet spare the skin from burning, thus providing a safe and permanent method of hair removal for patients with different skin colors, hair colors and hair textures.

Another advantage of the present invention is that it provides for an improved laser apparatus, controlled by a sequence control device, and a fiber optic cable which sequentially emits a defined pulse group having pulses of coherent light energy from the fiber optic cable for permanently removing a plurality of hair follicles from the skin area of a patient.

Another advantage of the present invention is that it provides for an improved laser apparatus having a handpiece for ease of use by the operator in directing the defined pulse group of laser pulses at the skin to rapidly remove large areas of hair on almost any body area, such as on the face, hands, arms, legs, breasts, stomach and the like, where such treatment provides a low discomfort level to the patient.

Another advantage of the present invention is that it provides a laser apparatus and a sequence control device for emitting laser energy through a common optical delivery system which delivers a defined pulse group of sequential pulses from the laser apparatus.

Another advantage of the present invention is that it provides for an improved method for adjusting the defined pulse group with regard to the number of pulses, pulse width, the time delay between pulses, and the energy level of each pulse, to customize the treatment and the energy delivered to the spot being treated according to skin color, hair color, hair texture (diameter) and the anatomic site being treated.

Another advantage of the present invention is that it provides for safe and permanent hair removal in a wider range of patients having different skin colors, such as a light skin color for Caucasians, a medium skin color for Hispanics, American Indians, Eastern Mediterranean-types, and a dark skin color for Africans and Afro-Americans.

Another advantage of the present invention is that it provides for safe and permanent hair removal in a wider range of patients having different hair colors and different hair textures. Such hair colors include blond hair; red hair; light, medium and dark brown hair; and black hair; and having hair texture (diameter) of fine or coarse hair. Generally, the present invention will accommodate all persons having hair which is darker than their skin.

Another advantage of the present invention is that it provides a delay between laser pulses which is much shorter than the thermal relaxation time of the hair being treated, so the hair does not cool off between pulses.

Another advantage of the present invention is that it provides a method and laser apparatus wherein the delay between laser pulses is so short that less energy has to be transmitted to the hair to cause permanent hair loss.

Another advantage of the present invention is that it provides for an improved laser apparatus and method that is easy to use, and the laser apparatus is durable, light-weight and easily maintained.

Another advantage of the present invention is that it provides for an improved laser apparatus that provides a wider beam area (spot size on the skin) by utilizing a laser apparatus and a sequence control device for delivering enough laser energy to each spot allowing the spot size to be made larger for faster treatment.

Another advantage of the parametrically defined pulse group (PDPG) of the present invention is that it allows for laser hair removal to be successful in clinical situations where it previously was impossible; and it allows for both greater efficacy and greater safety by taking advantage of thermodynamic differences between hair follicles and epidermis when both are simultaneously irradiated by the laser apparatus.

A further advantage of the present invention is that it provides for an improved laser apparatus that is simple to manufacture and assemble in an economical manner, and is cost effective for the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A laser apparatus for permanently removing a plurality of hair follicles from the skin of a patient, capable of producing an emission of laser energy in the form of a group of pulses having defined parameters, being a defined pulse group, comprising:
    a) a housing having a laser apparatus for emitting a defined pulse group of 2 to 15 pulses of coherent light energy with each pulse having a pulse duration in the range of 1.2 to 22 ms per pulse;
    b) light transmission means connected to said laser apparatus for emitting said defined pulse group of pulses of coherent light energy to the skin of a patient;
    c) means for controlling said laser apparatus to emit said defined pulse group of pulses of coherent light energy sequentially, with a time delay of less than 20 milliseconds between each of said pulses; and
    d) a handpiece for holding a section of said light transmission means for directing said defined pulse group of coherent light energy to a selected spot of the patient's skin to remove the plurality of hair follicles.

2. A laser apparatus in accordance with claim 1, wherein said light transmission means includes a multi-strand fiber optic bundle for transmitting said defined pulse group of coherent light energy.

3. A laser apparatus in accordance with claim 1, wherein said light transmission means includes articulated arms having at least two movable sections with mirrors for transmitting said defined pulse group of coherent light energy.

4. A laser apparatus in accordance with claim 1, wherein said laser apparatus is selected from the group consisting of a ruby laser, an alexandrite laser, a diode laser, an infrared laser, and a laser pumped dye laser.

5. A laser apparatus in accordance with claim 1, wherein said laser apparatus is a single laser for emitting multiple pulses having defined parameters, being a defined pulse group.

6. A laser apparatus in accordance with claim 1, wherein said laser apparatus is two or more lasers synchronized for emitting multiple pulses having defined parameters, being a defined pulse group.

7. A laser apparatus in accordance with claim 1, wherein said handpiece further includes cooling means for cooling a selected spot on the patient's skin.

8. A laser apparatus in accordance with claim 7, wherein said cooling means includes a cooling semi-conductor device.

9. A laser apparatus in accordance with claim 7, wherein said cooling means includes a cooling gel device, ice or cryogen-cooled sapphire crystals.

10. A laser apparatus in accordance with claim 7, wherein said cooling means includes a cooling thermoelectric device.

11. A laser apparatus in accordance with claim 10, wherein said cooling thermoelectric device includes a sapphire crystal that engages the skin, a heat sink, first and second rows of conductor spheres, and an evacuated sealed chamber.

12. A laser apparatus in accordance with claim 10, wherein said cooling thermoelectric device includes a sapphire crystal that engages the skin, a heat sink, a first ceramic spacer, a row of semi-conductor spheres, a second ceramic spacer, and an evacuated sealed chamber.

13. A method of removing hair from the skin of a patient using a laser apparatus capable of producing an emission of laser energy in the form of a group of pulses having defined parameters, being a defined pulse group and using an optical delivery system, comprising the steps of:

a) controlling said laser apparatus in each emission of laser energy to emit a defined pulse group of 2 to 15 pulses of coherent light energy;
b) emitting said defined pulse group of pulses of coherent light energy through an optical delivery system to the same spot on the skin of the patient;
c) irradiating the same spot on the skin containing the hair to be removed with said defined pulse group of coherent light energy transmitted through said optical delivery system from said laser apparatus; and
d) controlling said laser apparatus in each emission of laser energy to emit said defined pulse group through said optical delivery system, said defined pulse group having 2 to 15 pulses at a wavelength in the range of 550 to 1200 nm, each pulse at a power level in the range of 2 to 35 Joules/cm$^2$ per pulse, each pulse having a pulse duration in the range of 1.2 to 22 milliseconds per pulse, each pulse having a beam diameter on the treatment area in the range of 4 to 50 millimeters, said defined pulse group having a total fluence in the range of 4 to 100 Joules/cm$^2$, and a repetition rate of said laser apparatus between successive defined pulse groups being 500 to 2000 milliseconds; and
e) cooling the skin after said defined pulse group, wherein the step of cooling is performed by spraying cryogen on the patient's skin.

14. A method of removing hair from the skin of the patient in accordance with claim 13, wherein said step of cooling starts within 10 to 20 ms after the completion of said defined pulse group, and wherein said spraying step has a duration of 5 to 50 ms.

15. A method of removing hair from the skin of the patient in accordance with claim 13, further including the step of cooling the skin before emitting said defined pulse group.

16. A method of removing hair from the skin of the patient in accordance with claim 13, further including the step of cooling the skin between pulses of said defined pulse group.

17. A method of removing hair from the skin of a patient using a laser apparatus capable of producing an emission of laser energy in the form of a group of pulses having defined parameters, being a defined pulse group and using an optical delivery system, comprising the steps of:
a) controlling said laser apparatus in each emission of laser energy to emit a defined pulse group of 2 to 12 pulses of coherent light energy;
b) emitting said defined pulse group of pulses of coherent light energy through an optical delivery system to the same spot on the skin of the patient;
c) irradiating the same spot on the skin containing the hair to be removed with said defined pulse group of coherent light energy transmitted through said optical delivery system from said laser apparatus; and
d) controlling said laser apparatus in each emission of laser energy to emit said defined pulse group through said optical delivery system, said defined pulse group having 2 to 15 pulses at a wavelength in the range of 550 to 1200 nm, each pulse at a power level in the range of 2 to 35 Joules/cm$^2$ per pulse, each pulse having a pulse duration in the range of 1.2 to 22 milliseconds per pulse, each pulse having a beam diameter on the treatment area in the range of 4 to 50 millimeters, said defined pulse group having a total fluence in the range of 4 to 100 Joules/cm$^2$, and a repetition rate of said laser apparatus between successive defined pulse groups being 500 to 2000 milliseconds; and
e) cooling the skin during at least one delay between pulses of said defined pulse group, wherein said at least one delay between pulses is longer to accommodate said cooling step, and wherein the step of cooling is performed by spraying cryogen on the patient's skin.

18. A method of removing hair from the skin of the patient in accordance with claim 17, wherein said longer pulse delay is in the range of 5 to 50 ms to accommodate said cooling step.

19. A method of removing hair from the skin of the patient in accordance with claim 17, further including the step of cooing the skin before emitting said defined pulse group.

20. A method of removing hair from the skin of the patient in accordance with claim 17, further including the step of cooling the skin after emitting said defined pulse group.

21. A method of removing hair from the skin of a patient having dark colored skin using a laser apparatus capable of producing an emission of laser energy in the form of a group of pulses having defined parameters, being a defined pulse group and using an optical delivery system, comprising the steps of:
a) controlling said laser apparatus in each emission of laser energy to emit a defined pulse group of 2 to 12 pulses of coherent light energy;
b) emitting said defined pulse group of pulses of coherent light energy through an optical delivery system to the same spot on the skin of the patient;
c) irradiating the same spot on the skin containing the hair to be removed with said defined pulse group of coherent light energy transmitted through said optical delivery system from said laser apparatus; and
d) controlling said laser apparatus in each emission of laser energy to emit said defined pulse group through said optical delivery system, said defined pulse group having 2 to 12 pulses at a wavelength in the range of 550 to 1200 nm having a delay between pulses within said defined pulse group in the range of 2 to 20 milliseconds, each pulse at a power level in the range of 1.5 to 10 Joules/cm$^2$ per pulse, having a pulse duration in the range of 1.5 to 22 milliseconds per pulse, each pulse having a beam diameter on the treatment area in the range of 4 to 50 millimeters, said defined pulse group having a total fluence in the range of 4 to 50 Joules/cm$^2$, and a repetition rate of said laser apparatus between successive defined pulse groups being 500 to 2000 milliseconds.

22. A method of removing hair from the skin of a patient having dark colored skin in accordance with claim 21, wherein the patient has coarse, medium brown hair, and wherein said step of emitting said defined pulse group to the patient having coarse, medium brown hair includes emitting said defined pulse group having 4 to 8 pulses having a delay between pulses in the range of 2 to 14 milliseconds, each pulse having a pulse duration in the range of 4 to 10 milliseconds, and having a total fluence in the range of 18 to 40 Joules/cm$^2$.

23. A method of removing hair from the skin of a patient having dark colored skin in accordance with claim 21, wherein the patient has fine, black hair, and wherein said step of emitting said defined pulse group to the patient having fine, black hair includes emitting said defined pulse group having 2 to 10 pulses having a delay between pulses in the range of 4 to 16 milliseconds, each pulse having a pulse duration in the range of 4 to 12 milliseconds, and having a total fluence of 18 to 40 Joules/cm$^2$.

24. A method of removing hair from the skin of a patient having dark colored skin in accordance with claim 21, wherein the patient has coarse, black hair, and wherein said step of emitting said defined pulse group to the patient having fine, black hair includes emitting said defined pulse group having 4 to 15 pulses having a delay between pulses in the range of 6 to 20 milliseconds, each pulse having a pulse duration in the range of 5 to 22 milliseconds, and having a total fluence of 15 to 40 Joules/cm$^2$.

25. A method of removing hair from the skin of the patient having dark colored skin in accordance with claim 21, further including the step of cooling the skin during said defined pulse group and/or after said defined pulse group.

26. A method of removing hair from the skin of the patient having dark colored skin in accordance with claim 21, wherein said laser apparatus is selected from the group consisting of a ruby laser, an alexandrite laser, a diode laser, an infrared laser, and a laser pumped dye laser.

27. A method of removing hair from the skin of a patient having medium colored skin using a laser apparatus capable of producing an emission of laser energy in the form of a group of pulses having defined parameters, being a defined pulse group and using an optical delivery system, comprising the steps of:
  a) controlling said laser apparatus in each emission of laser energy to emit a defined pulse group of 2 to 12 pulses of coherent light energy;
  b) emitting said defined pulse group of pulses of coherent light energy through an optical delivery system to the same spot on the skin of the patient;
  c) irradiating the same spot on the skin containing the hair to be removed with said defined pulse group of coherent light energy transmitted through said optical delivery system from said laser apparatus; and
  d) controlling said laser apparatus in each emission of laser energy to emit said defined pulse group through said optical delivery system, said defined pulse group having 2 to 12 pulses at a wavelength in the range of 550 to 1200 nm having a delay between pulses within said defined pulse group in the range of 1 to 10 milliseconds, each pulse at a power level in the range of 2 to 15 Joules/cm$^2$ per pulse, having a pulse duration in the range of 1.5 to 6 milliseconds per pulse, each pulse having a beam diameter on the treatment area in the range of 4 to 50 millimeter, said defined pulse group having a total fluence in the range of 4 to 50 Joules/cm$^2$, and a repetition rate of said laser apparatus between successive defined pulse groups being 500 to 2000 milliseconds.

28. A method of removing hair from the skin of a patient having medium colored skin in accordance with claim 27, wherein the patient has fine, light brown hair, and wherein said step of emitting said defined pulse group to the patient having fine, light brown hair includes emitting said defined pulse group having 3 to 6 pulses having a delay between pulses in the range of 1 to 4 milliseconds, each pulse having a pulse duration in the range of 1.5 to 4 milliseconds, and having a total fluence in the range of 30 to 50 Joules/cm$^2$.

29. A method of removing hair from the skin of a patient having medium colored skin in accordance with claim 27, wherein the patient has coarse, light brown hair, and wherein said step of emitting said defined pulse group to the patient having coarse, light brown hair includes emitting said defined pulse group having 3 to 8 pulses having a delay between pulses in the range of 3 to 6 milliseconds, each pulse having a pulse duration in the range of 1.5 to 4 milliseconds, and having a total fluence in the range of 30 to 50 Joules/cm$^2$.

30. A method of removing hair from the skin of a patient having medium colored skin in accordance with claim 27, wherein the patient has fine, medium brown hair, and wherein said step of emitting said defined pulse group to the patient having fine, medium brown hair includes emitting said defined pulse group having 3 to 8 pulses having a delay between pulses in the range of 2 to 5 milliseconds, each pulse having a pulse duration in the range of 1.5 to 4 milliseconds, and having a total fluence in the range of 30 to 50 Joules/cm$^2$.

31. A method of removing hair from the skin of a patient having medium colored skin in accordance with claim 27, wherein the patient has coarse, medium brown hair, and wherein said step of emitting said defined pulse group to the patient having coarse, medium brown hair includes emitting said defined pulse group having 3 to 8 pulses having a delay between pulses in the range of 4 to 6 milliseconds, each pulse having a pulse duration in the range of 2 to 5 milliseconds, and having a total fluence in the range of 30 to 50 Joules/cm$^2$.

32. A method of removing hair from the skin of a patient having medium colored skin in accordance with claim 27, wherein the patient has fine, black hair, and wherein said step of emitting said defined pulse group to the patient having fine, black hair includes emitting said defined pulse group having 3 to 10 pulses having a delay between pulses in the range of 2 to 5 milliseconds, each pulse having a pulse duration in the range of 2 to 5 milliseconds, and having a total fluence in the range of 24 to 50 Joules/cm$^2$.

33. A method of removing hair from the skin of a patient having medium colored skin in accordance with claim 27, wherein the patient has coarse, black hair, and wherein said step of emitting said defined pulse group to the patient having coarse, black hair includes emitting said defined pulse group having 3 to 12 pulses having a delay between pulses in the range of 4 to 6 milliseconds, each pulse having a pulse duration in the range of 4 to 6 milliseconds, and having a total fluence in the range of 20 to 50 Joules/cm$^2$.

34. A method of removing hair from the skin of the patient having medium colored skin in accordance with claim 27, further including the step of cooling the skin during said defined pulse group and/or after said defined pulse group.

35. A method of removing hair from the skin of the patient having medium colored skin in accordance with claim 34, wherein the step of cooling is performed between pulses of said defined pulse group, and wherein at least one delay between pulses is longer to accommodate said cooling step, and cryogen is sprayed on the patient's skin.

36. A method of removing hair from the skin of the patient having medium colored skin in accordance with claim 34, wherein the step of cooling is performed after pulses of said defined pulse group and cryogen is sprayed on the patient's skin.

37. A method of removing hair from the skin of the patient having medium colored skin in accordance with claim 27, wherein said laser apparatus is selected from the group consisting of a ruby laser, an alexandrite laser, a diode laser, an infrared laser, and a laser pumped dye laser.

38. A method of removing hair from the skin of a patient having light colored skin using a laser apparatus capable of producing an emission of laser energy in the form of a group of pulses having defined parameters, being a defined pulse group and using an optical delivery system, comprising the steps of:
  a) controlling said laser apparatus in each emission of laser energy to emit a defined pulse group of 2 to 10 pulses of coherent light energy;
  b) emitting said defined pulse group of pulses of coherent light energy through an optical delivery system to the same sport on the skin of the patient;

c) irradiating the same spot on the skin containing the hair to be removed with said defined pulse group of coherent light energy transmitted through said optical delivery system from said laser apparatus; and d) controlling said laser apparatus in each emission of laser energy to emit said defined pulse group through said optical delivery system, said defined pulse group having 2 to 10 pulses at a wavelength in the range of 550 to 1200 nm having a delay between pulses within said defined pulse group in the range of 0.5 to 6 milliseconds, each pulse at a power level in the range of 2 to 35 Joules/cm$^2$, each pulse having a pulse duration in the range of 1.2 to 10 milliseconds, each pulse having a beam diameter on the treatment area in the range of 4 to 50 millimeters, said defined pulse group having a total fluence in the range of 4 to 100 Joules/cm$^2$, and a repetition rate of said laser apparatus between successive defined pulse groups being 500 to 2000 milliseconds.

39. A method of removing hair form the skin of the patient having light colored skin in accordance with claim 38, wherein said laser apparatus is selected from the group consisting of a ruby laser, an alexandrite laser, a diode laser, an infrared laser, and a laser pumped dye laser.

40. A method of removing hair from the skin of a patient having light colored skin in accordance with claim 38, wherein the patient has fine, light brown hair, and wherein said step of emitting said defied pulse group to the patient having fine, light brown hair includes emitting said defined pulse group having 2 to 4 pulses having a delay between pulses in the range of 0.5 to 2 milliseconds, each pulse having a pulse duration in the range of 1.2 to 4 milliseconds, and having a total fluence in the range of 40 to 100 Joules/cm$^2$.

41. A method of removing hair firm the skin of a patient having light colored skin in accordance with claim 38, wherein the patient has coarse, light brown hair, and wherein said step of emitting said defined pulse group to the patient having coarse, light brown hair includes emitting said defined pulse group having 2 to 4 pulses having a delay between pulses in the range of 1 to 2 milliseconds, each pulse having a pulse duration in the range of 1.2 to 4 milliseconds, and having a total fluence in the range of 40 to 100 Joules/cm$^2$.

42. A method of removing hair from the skin of a patient having light colored skin in accordance with claim 38, wherein the patient has fine, medium brown hair, and wherein said step of emitting said defined pulse group to the patient having fine, medium brown hair includes emitting said defined pulse group having 2 to 4 pulses having a delay between pulses in the range of 1 to 2 milliseconds, each pulse having a pulse duration in the range of 1.5 to 4 milliseconds, and having a total fluence in the range of 40 to 100 Joules/cm$^2$.

43. A method of removing hair from the skin of a patient having light colored skin in accordance with claim 38, wherein the patient has coarse, medium brown hair, and wherein said step of emitting said defined pulse group to the patient having coarse, medium brown hair includes emitting said defined pulse group having 2 to 6 pulses having a delay between pulses in the range of 2 to 4 milliseconds, each pulse having a pulse duration in the range of 1.5 to 4 milliseconds, and having a total fluence in the range of 40 to 100 Joules/cm$^2$.

44. A method of removing hair from the skin of a patient having light colored skin in accordance with claim 38, wherein the patient has fine, black hair, and wherein said step of emitting said defined pulse group to the patient having fine, black hair includes emitting said defined pulse group having 2 to 6 pulses having a delay between pulses in the range of 1 to 3 milliseconds, each pulse having a pulse duration in the range of 1.5 to 4 milliseconds, and having a total fluence in the range of 40 to 100 Joules/cm$^2$.

45. A method of removing hair from the skin of a patient having light colored skin in accordance with claim 38, wherein the patient has coarse, black hair, and wherein said step of emitting said defined pulse group to the patient having coarse, black hair includes emitting said defined pulse group having 2 to 10 pulses having a delay between pulses in the range of 2 to 4 milliseconds, each pulse having a pulse duration in the range of 2 to 6 milliseconds, and having a total fluence in the range of 30 to 100 Joules/cm$^2$.

46. A method of removing hair from the skin of the patient having light colored skin in accordance with claim 38, further including the step of cooling the skin during said defined pulse group and/or after said defined pulse group.

47. A method of removing hair from the skin of the patient having light colored skin in accordance with claim 46, wherein the step of cooling is performed between pulses of said defined pulse group, and wherein at least one delay between pulses is longer to accommodate said cooling step, and cryogen is sprayed on the patient's skin.

48. A method of removing hair from the skin of the patient having light colored skin in accordance with claim 46, wherein the step of cooling is performed after pulses of said defined pulse group and cryogen is sprayed on the patient's skin.

49. A method of removing hair from the skin of the patient having dark colored skin in accordance with claim 46, wherein the step of cooling is performed between pulses of said defined pulse group, and wherein at least one delay between pulses is longer to accommodate said cooling step, and cryogen is sprayed on the patient's skin.

50. A method of removing hair from the skin of the patient having dark colored skin in accordance with claim 46, wherein the step of cooling is performed after pulses of said defined pulse group and cryogen is sprayed on the patient's skin.

* * * * *